US010980896B2

(12) United States Patent
Cepko et al.

(10) Patent No.: US 10,980,896 B2
(45) Date of Patent: Apr. 20, 2021

(54) METHODS AND COMPOSITIONS FOR INHIBITING OXIDATIVE STRESS

(71) Applicant: President and Fellows of Harvard College, Cambridge, MA (US)

(72) Inventors: Constance L. Cepko, Newton, MA (US); Wenjun Xiong, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 56 days.

(21) Appl. No.: 15/032,426

(22) PCT Filed: Oct. 29, 2014

(86) PCT No.: PCT/US2014/062917
§ 371 (c)(1),
(2) Date: Apr. 27, 2016

(87) PCT Pub. No.: WO2015/066190
PCT Pub. Date: May 7, 2015

(65) Prior Publication Data
US 2016/0279265 A1    Sep. 29, 2016

Related U.S. Application Data

(60) Provisional application No. 61/896,805, filed on Oct. 29, 2013.

(51) Int. Cl.
| *A61K 48/00* | (2006.01) |
| *A61K 45/06* | (2006.01) |
| *A61K 31/7115* | (2006.01) |
| *A61K 38/17* | (2006.01) |
| *A61K 38/44* | (2006.01) |

(52) U.S. Cl.
CPC ...... *A61K 48/0058* (2013.01); *A61K 31/7115* (2013.01); *A61K 38/1709* (2013.01); *A61K 38/446* (2013.01); *A61K 45/06* (2013.01); *A61K 48/005* (2013.01); *A61K 48/0075* (2013.01); *C12N 2750/14143* (2013.01); *C12Y 115/01001* (2013.01); *Y02A 50/30* (2018.01)

(58) Field of Classification Search
None
See application file for complete search history.

(56) References Cited

U.S. PATENT DOCUMENTS

| 2002/0049176 A1* | 4/2002 | Anderson | C07K 14/4705 514/44 R |
| 2007/0203083 A1 | 8/2007 | Mootha et al. | |
| 2008/0274093 A1* | 11/2008 | Johnson | C12N 5/0618 424/93.21 |
| 2011/0250300 A1* | 10/2011 | Biswal | A01K 67/027 424/752 |
| 2012/0108654 A1* | 5/2012 | Campochiaro | A61K 38/446 514/44 R |
| 2012/0232130 A1 | 9/2012 | Cepko et al. | |
| 2013/0288985 A1* | 10/2013 | Jurkunas | A61K 9/0048 514/20.8 |

FOREIGN PATENT DOCUMENTS

| WO | WO-00/54595 A1 | 9/2000 |
| WO | WO-08/063802 A2 | 5/2008 |
| WO | WO-08/097596 A2 | 8/2008 |

OTHER PUBLICATIONS

Lebherz et al., J Gene Med, 2008, vol. 10(4), pp. 375-382.*
Miyoshi et al., PNAS, 1997, vol. 94, pp. 10319-10323.*
Komeima et al (PNAS, 2006. vol. 103, No. 30 pp. 11300-11305).*
Boatright et al (Molecular Vision, 1997, vol. 3, No. 15).*
Kennedy et al (Experimental Eye Research 2003. vol. 76, pp. 257-260).*
Zhou et al (Genomics, 2001, vol. 73, pp. 86-97).*
Koch et al. "Gene therapy restores vision and delays degeneration in the CNGB1 −/− mouse model of retinitis pigmentosa," Human Molecular Genetics, Jul. 16, 2012, vol. 21, No. 20, p. 4486-4496.
Zhu et al. "Hydroxytyrosol protects against oxidative damage by simultaneous activation of mitochondria! biogenesis and phase II detoxifying enzyme systems in retinal pigment epithelial cells," Journal of Nutritional Biochemistry, Feb. 9, 2010, vol. 21, No. 11, pp. 1089-1098.
Clark et al., "Transcribe to Survive: Transcriptional Control of Antioxidant Defense Programs for Neuroprotection in Parkinson's Disease," Antioxidants & Redox Signaling. Jan. 2009, 11(3): 509-528.
International Search Report and Written Opinion from PCT/US2014/062917, dated Feb. 12, 2015.
Usui et al., "Increased Expression of Catalase and Superoxide Dismutase 2 Reduces Cone Cell Death in Retinitis Pigmentosa,"*Molecular Therapy*, vol. 17 :5, 2009, p. 778-786.
Liu et al., "Effects of antioxidant gene therapy on retinal neurons and oxidative stress in a model of retinal ischemia/reperfusion," Free Radical Biology & Medicine, vol. 52(5), 2011, pp. 909-915.
Rex et al., "Adenovirus-Mediated Delivery of Catalase to Retinal Pigment Epithelial Cells Protects Neighboring Photoreceptors from Photo-Oxidative Stress," Hum Gene Ther. Oct. 2004; 15(10): 960-967.
Himoi et al., "Critical role of Nrf2 in oxidative stress-induced retinal ganglion cell death," J. Neurochem. (2013) 127:5, 669-680.
Natkunarajah et al., "Assessment of ocular transduction using single-stranded and self-complementary recombinant adeno-associated virus serotype 2/8, " Gene Therapy (2008) 15, 463-467.
Punzo et al., "Loss of Daylight Vision in Retinal Degeneration: Are Oxidative Stress and Metabolic Dysregulation to Blame?," J Biol Chem, 2012, vol. 287, No. 3, p. 1642.

(Continued)

*Primary Examiner* — Celine X Qian
(74) *Attorney, Agent, or Firm* — McCarter & English, LLP; Maria Laccotripe Zacharakis; Deborah L. Nagle

(57) ABSTRACT

The present invention is directed to methods for the treatment or prevention of oxidative stress in a cell, e.g., photoreceptor cell, and methods for the treatment and prevention of disorders associated therewith by the administration of an agent, e.g., a nucleic acid molecule, which increases the expression and/or activity of an antioxidant defense protein.

7 Claims, 26 Drawing Sheets

(56) References Cited

OTHER PUBLICATIONS

Zheng et al., "Improvement of Retinal Vascular Injury in Diabetic Rats by Statins Is Associated With the Inhibition of Mitochondrial Reactive Oxygen Species Pathway Mediated by Peroxisome Proliferator-Activated Receptor γ Coactivator 1α," Diabetes Sep. 2010; 59(9): 2315-2325.
Egger et al., "PGC-1a Determines Light Damage Susceptibility of the Murine Retina," PLoS One, Feb. 2012, vol. 7(2):e31272.
Kanninen et al., "Intrahippocampal injection of a lentiviral vector expressing Nrf2 improves spatial learning in a mouse model of Alzheimer's disease", PNAS, vol. 106(38):16505-16510, Sep. 22, 2009.
Chorley et al., "Identification of novel NRF2-regulated genes by ChIP-Seq: influence on retinoid X receptor alpha", Nucleic Acids Research, vol. 40(15):7416-7429, 2012.
Mazzuferi et al., "Nrf2 Defense Pathway: Experimental Evidence for Its Protective Role in Epilepsy", Annals of Neurology, vol. 73(6):560-568, Jun. 2013.
Egger et al., "PGC-1a Determines Light Damage Susceptibility of the Murine Retina", PLoS One, vol. 7(2), e31272, Feb. 2012.
Karkkainen et al., "Nrf2 Regulates Neurogenesis and Protects Neural Progenitor Cells Against Ab Toxicity", Stem Cells, 32:1904-1916, 2014.
Fujita et al., "Spatially and Temporally Regulated NRF2 Gene Therapy Using Mcp-1 Promoter in Retinal Ganglion Cell Injury", Molecular Therapy: Methods & Clinical Development, vol. 5:130-141, 2017.
Mills et al., "Emerging Understanding of the Mechanism of Action for Dimethyl Fumarate in the Treatment of Multiple Sclerosis", Frontiers in Neurology, vol. 9(5):1-8, Jan. 2018.

\* cited by examiner

METHODS AND COMPOSITIONS FOR INHIBITING OXIDATIVE STRESS

RELATED APPLICATIONS

This application is a 35 U.S.C. § 371 national stage filing of International Application No. PCT/US2014/062917, filed on Oct. 29, 2014, which in turn claims the benefit of priority to U.S. Provisional Patent Application No. 61/896,805, filed on Oct. 29, 2013. The entire contents of each of the foregoing applications are incorporated herein by reference.

STATEMENT REGARDING FEDERALLY SPONSORED RESEARCH OR DEVELOPMENT

This invention was made with Government support under contract EY023291-01 awarded by the National Institutes of Health. The government has certain rights in the invention.

BACKGROUND OF THE INVENTION

Cells can be compromised by genetic and environmental factors that lead to their malfunction and death. For example, in the retina, specialized sensory neurons, the photoreceptors (rods and cones), as well as retinal ganglion cells (RPG), the output neurons of the retina, are the neuronal cell types that can malfunction and die due to genetic and/or environmental reasons, leading to partial or complete loss of vision.

The retina contains two major types of light-sensitive photoreceptor cells, i.e., rod cells and cone cells. Cone cells are responsible for color vision and require brighter light to function, as compared to rod cells. There are three types of cones, maximally sensitive to long-wavelength, medium-wavelength, and short-wavelength light (often referred to as red, green, and blue, respectively, though the sensitivity peaks are not actually at these colors). Cones are mostly concentrated in and near the fovea. Only a small percentage of photoreceptors are cones in the periphery of the retina. Objects are seen most sharply in focus when their images fall on the cone-enriched spot, as when one looks at an object directly. Cone cells and rods are connected through intermediate cells in the retina to nerve fibers of the optic nerve. When rods and cones are stimulated by light, the nerves send off impulses through these fibers to the brain.

Reduced viability of cone cells is associated with various retinal disorders, in particular, retinitis pigmentosa. Retinitis pigmentosa is a family of inherited retinal degenerations (RD) that is currently incurable and frequently leads to blindness. Affecting roughly 1 in 3,000 individuals, it is the most prevalent form of RD caused by a single disease allele (see, e.g., RetNet). The phenotype is characterized by an initial loss of night vision due to the malfunction and death of rod photoreceptors, followed by a progressive loss of cones (Madreperla, S. A., et al. (1990) *Arch Ophthalmol* 108, 358-61). Additionally, retinitis pigmentosa is further characterized by, e.g., night blindness, progressive loss of peripheral vision, eventually leading to total blindness, ophthalmoscopic changes consisting of dark mosaic-like retinal pigmentation, attenuation of the retinal vessels, waxy pallor of the optic disc, and in the advanced forms, macular degeneration. Since cones are responsible for color and high acuity vision, it is their loss that leads to a reduction in the quality of life. In many cases, the disease-causing allele is expressed exclusively in rods; nonetheless, cone cell death follows rod cell death. Indeed, to date there is no known form of RD in humans or mice where rods die, and cones survive. In contrast, mutations in cone-specific genes result only in cone death.

Thus, there is a need in the art for therapies to prevent, treat, diagnose and prognose vision loss that results from decreased retinal cell function.

SUMMARY OF THE INVENTION

The present invention is directed to methods for inhibiting oxidative stress in a cell, e.g., a photoreceptor cell, as well as methods for treating or preventing a disorder associated with oxidative stress, e.g., oxidative stress of a photoreceptor cell. The present invention is based, at least in part, on the discovery that increased expression and/or activity of certain genes (genes encoding antioxidant defense proteins) in a photoreceptor cell undergoing oxidative stress can serve to fight oxidation and/or detoxify free radicals. In particular, the increased expression of genes encoding proteins involved in general up-regulation of the anti-oxidation program (e.g., transcription factors), as well as the increased expression of genes encoding antioxidant enzymes that detoxify free radicals have been shown to, increase photoreceptor viability.

Accordingly, the present invention provides methods for inhibiting oxidative stress of a photoreceptor cell, as well as methods for the treatment and/or prevention of disorders associated with cellular oxidative stress, for example, retinitis pigmentosa, by increasing the expression and/or activity of an antioxidant defense protein, including e.g., superoxide dismutase 2 (SOD2), catalase, peroxisome proliferator-activated receptor gamma coactivator 1-alpha (PGC1α), and nuclear factor erythroid 2-like 2 (Nrf2).

In one aspect, the present invention provides a method for inhibiting oxidative stress of a photoreceptor cell compromised by a retinal disorder. The method includes contacting the cell with an agent that increases the expression and/or activity of an antioxidant defense protein, thereby inhibiting oxidative stress of the photoreceptor cell.

In another aspect, the present invention provides a method for inhibiting oxidative stress of a cell. The method includes contacting the cell with nucleic acid molecules that encode catalase, SOD2, PGC1α, and/or Nrf2, or any combination or sub-combinations thereof, thereby inhibiting oxidative stress in a cell. In some embodiments, the cell is a photoreceptor cell such as, e.g., cone and/or rod cell. In some embodiments, the cell is a neuronal cell. In certain embodiments, the cell is a neuronal cell, a defect in which gives rise to a neurological disorder.

In another aspect, the present invention provides a method for prolonging the viability of a photoreceptor cell compromised by a retinal disorder. The method includes contacting the cell with an agent that increases the expression and/or activity of an antioxidant defense protein, thereby inhibiting oxidative stress of the photoreceptor cell. In certain embodiments, the viability of a photoreceptor cell is prolonged, e.g., for about 1 week, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 2 years, about 3 years, about 4 years, about 5 years, about 10 years, about 15, years, about 20 years, about 25 years, about 30 years, about 40 years, about 50 years, about 60 years, about 70 years, and about 80 years.

In another aspect, the present invention provides a method for treating or preventing a retinal disorder in a subject. The method includes administering to the subject an agent that increases the expression and/or activity and of an antioxidant defense protein, thereby treating or preventing the ocular disorder.

In yet another aspect, the present invention provides a method for treating or preventing retinitis pigmentosa in a subject. The method includes administering to the subject an agent that increases the expression and/or activity of an antioxidant defense protein, thereby treating or preventing retinitis pigmentosa in the subject.

In a further aspect, the present invention provides a method for treating or preventing a disorder associated with oxidative stress in a subject. The method includes administering to the subject one or more nucleic acid molecules that encode catalase, SOD2, PGC1α, and/or Nrf2, thereby treating or preventing a disorder associated with oxidative stress in the subject. In some embodiments, the disorder is an ocular disorder. In some embodiments, the disorder is a neurological disorder, e.g., Alzheimer's Disease, Parkinson Disease, Huntington's Disease, and Amyotrophic Lateral Sclerosis.

In any of the foregoing aspects of the invention, the increased expression of an antioxidant defense protein reduces the level of reactive oxygen species (ROS). In certain embodiments, ROS include, e.g., free radical species. In some embodiments, the antioxidant defense protein combats free radicals. In certain embodiments of the foregoing methods, the photoreceptor cell is a cone and/or rod cell.

In some embodiments, the ocular disorder is selected from the group consisting of retinitis pigmentosa, age related macular degeneration, cone rod dystrophy, rod cone dystrophy, and glaucoma. In one embodiment, the ocular disorder is a retinal disorder.

In certain embodiments of the foregoing methods, the ocular disorder is associated with decreased viability of cone cells and/or decreased viability of rod cells. In some embodiments, the ocular disorder is a genetic disorder. In other embodiments, the ocular disorder is not associated with blood vessel leakage and/or growth. In certain embodiments, the ocular disorder is not associated with diabetes and/or diabetic retinopathy. In further embodiments, the ocular disorder is not NARP (neuropathy, ataxia and retinitis pigmentosa).

In one embodiment of the foregoing methods, the agent is a nucleic acid molecule encoding an antioxidant defense protein. In certain embodiments, the nucleic acid molecule comprises an antioxidant defense gene. In some embodiments, the antioxidant defense gene encodes a transcription factor or an antioxidant enzyme. In particular embodiments, the antioxidant defense gene is selected from the group consisting of catalase, superoxide dismutase 2 (SOD2), peroxisome proliferator-activated receptor gamma coactivator 1-alpha (PGC1α), nuclear factor erythroid 2-like 2 (Nrf2), and any combination thereof.

Thus, any of the following combinations of antioxidant defense genes may be used in the methods of the invention: catalase; SOD2; PGC1α; nrf2; catalase and SOD2; SOD2 and PGC1α; PGC1α and nrf2; catalase and PGC1α; catalase and nrf2; SOD2 and nrf2; catalase, SOD2, and PGC1α; SOD2, PGC1α, and nrf2; catalase, PGC1α, and nrf2; catalase, SOD2, and nrf2; or catalase, SOD2, PGC1α, and nrf2.

In certain embodiments, the nucleic acid molecule is contained within a vector. In an exemplary embodiment, the vector is selected from the group consisting of a retroviral vector, an adenoviral vector, an adenoviral/retroviral chimera vector, an adeno-associated virus (AAV) vector, a herpes simplex viral I or II vector, a parvovirus vector, a reticuloendotheliosis virus vector, a poliovirus vector, a papillomavirus vector, a vaccinia virus vector, and a lentivirus vector. In one embodiment, the vector is an AAV vector, for example, an AAV 2/5 or an AAV 2/8 vector.

In the foregoing aspects of treating or preventing a retinal disorder, or specifically retinitis pigmentosa, the administration is intraocular administration. In exemplary embodiments, the intraocular administration is selected from the group consisting of intravitreal, subconjunctival, sub-tenon, periocular, retrobulbar, suprachoroidal, and intrascleral administration. In one embodiment, the intraocular administration is sub-retinal or intravitreal administration.

In another aspect, the present invention provides methods for treating or preventing retinitis pigmentosa in a subject. The methods include administering to the subject an isolated Nrf2 nucleic acid molecule, thereby treating or preventing retinitis pigmentosa in the subject.

In yet another aspect, the present invention provides methods for treating or preventing retinitis pigmentosa in a subject. The methods include administering to the subject an isolated Nrf2 nucleic acid molecule and an isolated PGC1α nucleic acid molecule, thereby treating or preventing retinitis pigmentosa in the subject.

In one embodiment, the nucleic acid molecule is contained within a vector, such as a vector selected from the group consisting of a retroviral vector, an adenoviral vector, an adenoviral/retroviral chimera vector, an adeno-associated virus (AAV) vector, a herpes simplex viral I or II vector, a parvovirus vector, a reticuloendotheliosis virus vector, a poliovirus vector, a papillomavirus vector, a vaccinia virus vector, and a lentivirus vector. In one embodiment, the vector is an AAV vector, e.g., an AAV 2/5 or an AAV 2/8 vector.

In one embodiment, the administration is intraocular administration, such as intravitreal, sub-retinal, subconjunctival, sub-tenon, periocular, retrobulbar, suprachoroidal, and intrascleral administration. In one particular embodiment, the intraocular administration is sub-retinal or intravitreal administration.

In one aspect, the present invention provides pharmaceutical compositions suitable for intraocular administration, comprising an isolated Nrf2 nucleic acid molecule.

In another aspect, the present invention provides pharmaceutical compositions suitable for intraocular administration, comprising an isolated Nrf2 nucleic acid molecule and an isolated PGC1α nucleic acid molecule.

In one embodiment, a therapeutically or prophylactically effective amount of the nucleic acid molecule is contained in the compositions suitable for intraocular administration.

In one aspect, the present invention provides compositions comprising a viral vector comprising a retinal cell-type specific promoter operably linked to a nucleic acid molecule encoding Nrf2.

In another aspect, the present invention provides compositions comprising a viral vector comprising a retinal cell-type specific promoter operably linked to a nucleic acid molecule encoding PGC1α.

In yet another aspect, the present invention provides compositions comprising a viral vector comprising a retinal cell-type specific promoter operably linked to a nucleic acid molecule encoding Nrf2 and PGC1α.

The retinal cell-type specific promoter may be a rod-specific promoter, a cone-specific promoter, and/or a rod- and cone-specific promoter.

In one embodiment, the composition is suitable for intraocular administration, e.g., sub-retinal or intravitreal administration.

Other features and advantages of the invention will be apparent from the following detailed description and claims

The right side of the graph shows the results from retinas injected with AAV-CMV-GFP+AAV-CMV-Nrf2 of rho−/− mice that were harvested at P100 for this experiment. Ten ganglion cells from each retina were measured for light-evoked activity. Peak firing rate (spikes/sec) of each ganglion cell was averaged over 20 trials of 1 second light stimulus (wavelength: 356 nm+505 nm, light intensity: 1010 photons cm−2 s−1).

ON, OFF and ON/OFF ganglion cells were included for this analysis. The average peaking firing rate (white line) of antioxidant AAV vectors treated retinas was higher compared to the control treated retinas, and the difference is statistically significant (p<0.05).

FIG. 15A-15B are photomicrographs demonstrating that overexpression of PGC1α and Nrf2 saves cone photoreceptors in central and middle retinas. Representative flat-mounted rd1 P50 retinas from control group (A; AAV-CMV-GFP treated) and antioxidant transcription factor group (B; AAV-CMV-GFP+AAV-CMV-PGC1α+AAV-CMV-Nrf2 treated) are shown. Cone photoreceptors were tracked by GFP (green). The boxes to the right of A and B are magnifications of an area 1.5 mm dorsal to the optic nerve head. Note the absence of GFP in the central and mid retina (highlighted by square) of the control animal (A). Many GFP positive cells are evident in the antioxidant transcription factor AAV treated retina (B).

Figure 16:
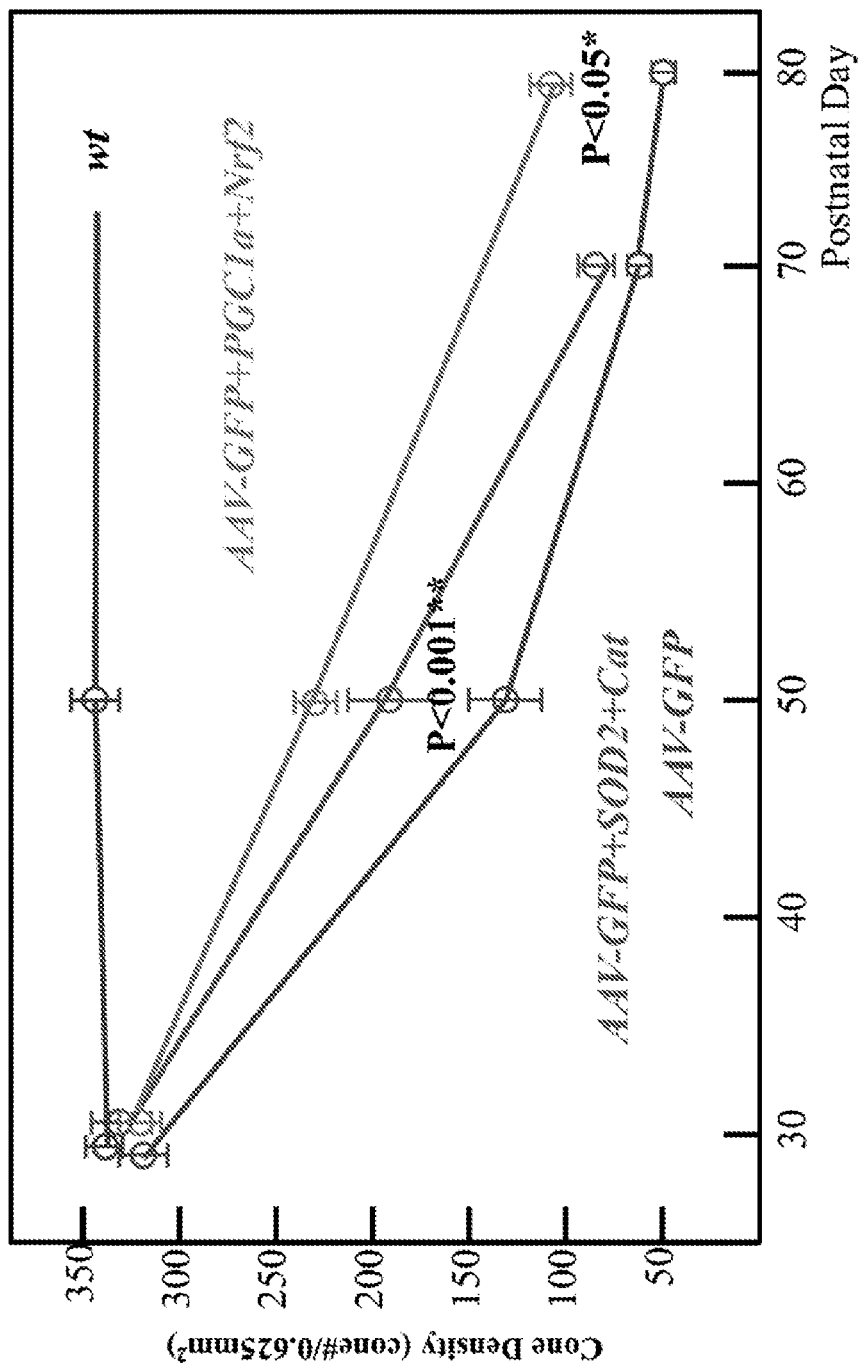

FIG. 16 demonstrates that overexpression of PGC1α and Nrf2 prolongs cone survival. The mean (±SEM) cone density of rd1 retinas treated with AAV-CMV-GFP+AAV-CMV-PGC1α+AAV-CMV-Nrf2 vectors at P30, P50 and P80 are shown (light gray line). The mean (±SEM) cone density was significantly greater (p<0.001) at P50 in the retinas overexpressing SOD2 and catalase compared to the control retinas with AAV-CMV-GFP. The mean cone density of PGC1α and Nrf2 treated retinas was significantly greater than that of control retinas (p<0.001) and that of SOD2 and catalase treated retinas (p<0.001) at P50, and it remained significantly higher than that of the control retinas (p<0.05) at P80.

Figure 17:
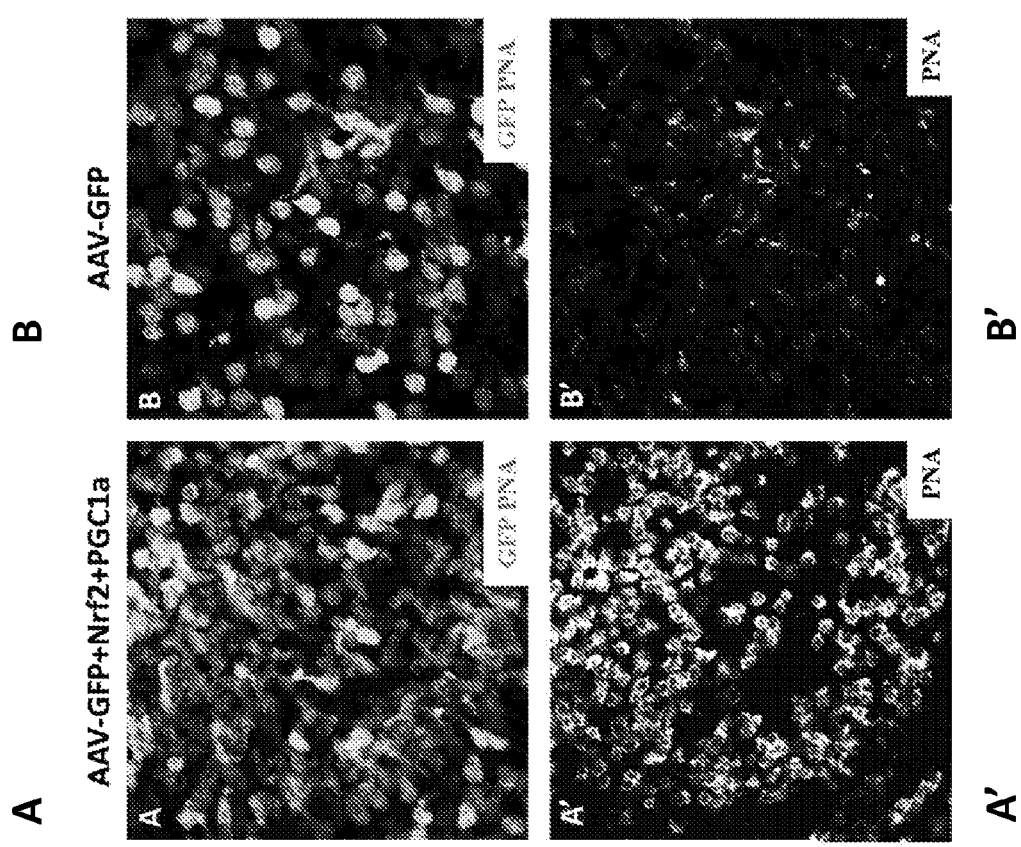
Figure 18:
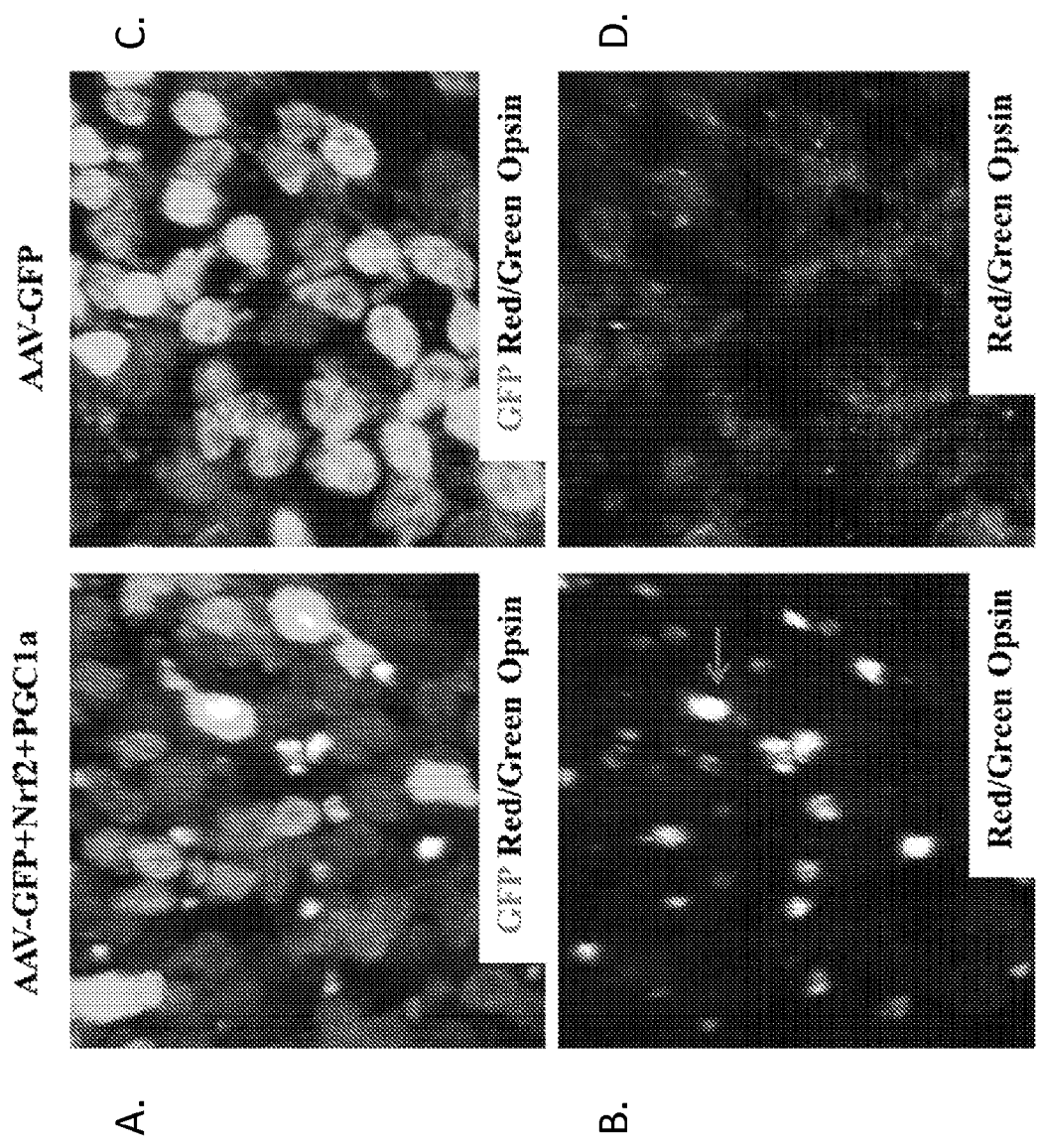

FIGS. 17A-17B demonstrate that overexpression of PGC1α and Nrf2 preserves outer segments (OS) and inner segments (IS) of cones in central retina. High magnification images of the mid dorsal regions of flat-mounted P30 WT and rd1 retinas infected with AAV vectors expressing PGC1a and Nrf2 (A, A'). Retinas were stained with anti PNA (A', B') to show cone outer segments (OS) and inner segments (IS), with more OS and IS present in the retinas treated with PGC1a and Nrf2 overexpression (A, A'), control rd1 retina lacked OS and IS (B, B').

FIGS. 18A-18D demonstrate that overexpression of Nrf2 and PGC1α preserves cone outer segments (OS). A and B are photomicrographs of outer segments infected with AAV-GFP+NRF2+PGC1α, and C and D are photomicrographs of outer segments infected with AAV-GFP. A and C are stained for GFP and red/green opsin and B and D are stained for red/green opsin. As shown in A and B, red/green opsin protein localized to the remaining cone outer segment structure, while it mislocalized to the cytoplasm of cell soma in the control retina. Arrow indicates an example of the cone outer segment.

Figure 19:
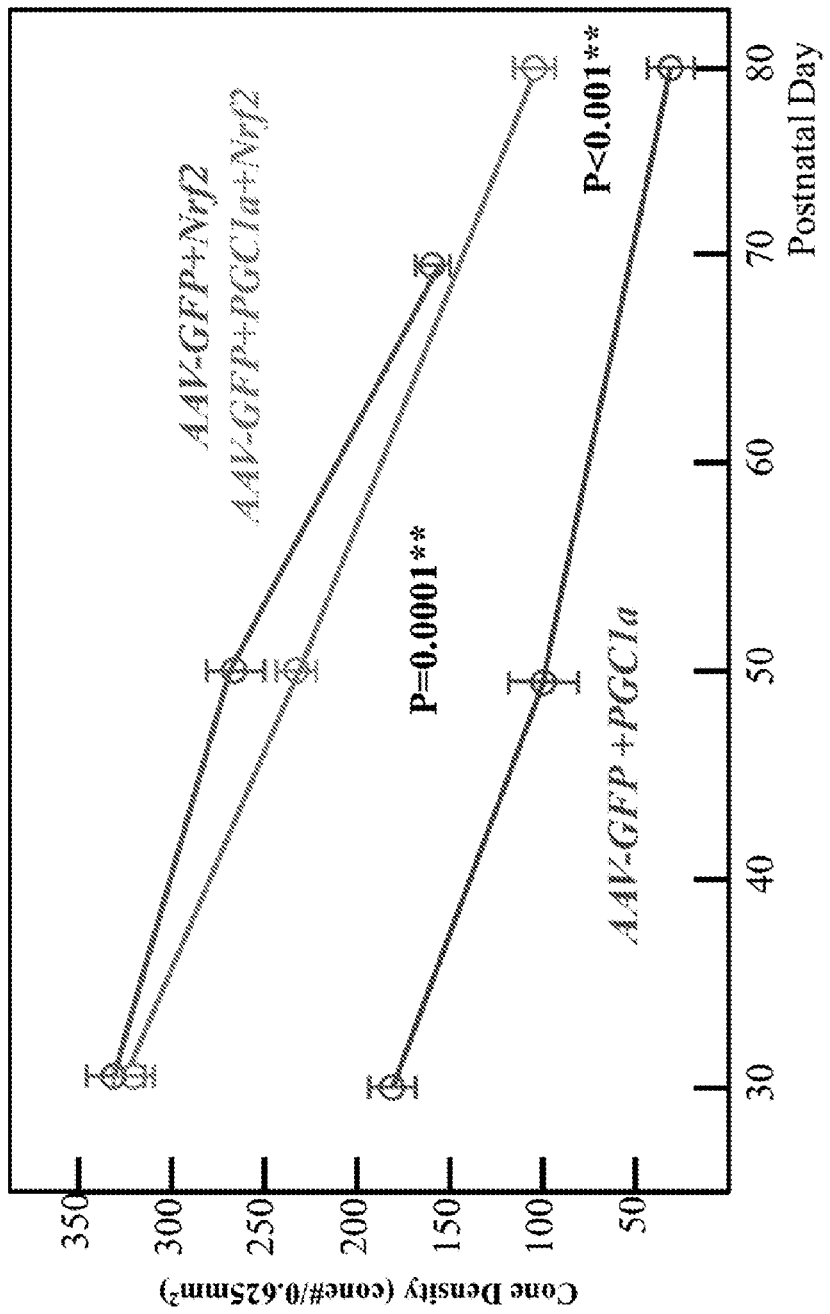

FIG. 19 is a graph demonstrating that overexpression of Nrf2 alone prolongs cone survival. The average cone densities in rd1 retinas infected with AAV vectors expressing GFP+PGC1α (lower line), GFP+Nrf2 (upper line) and GFP+PGC1α+Nrf2 (middle line) are shown. The mean cone density was greater in the retinas treated with AAV-CMV-GFP+AAV-CMV-Nrf2 than that in those treated with AAV vectors expressing AAV-CMV-GFP+AAV-CMV-PGC1α+AAV-CMV-Nrf2 at P50.

Figure 20:
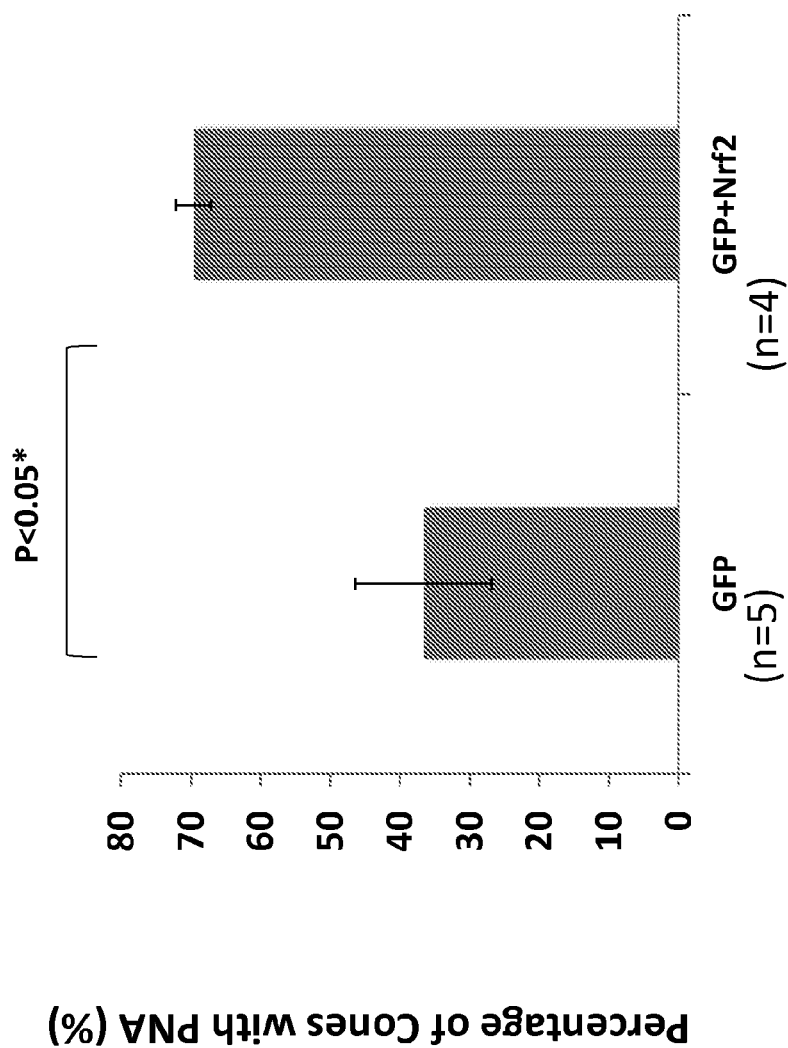
Figure 21:
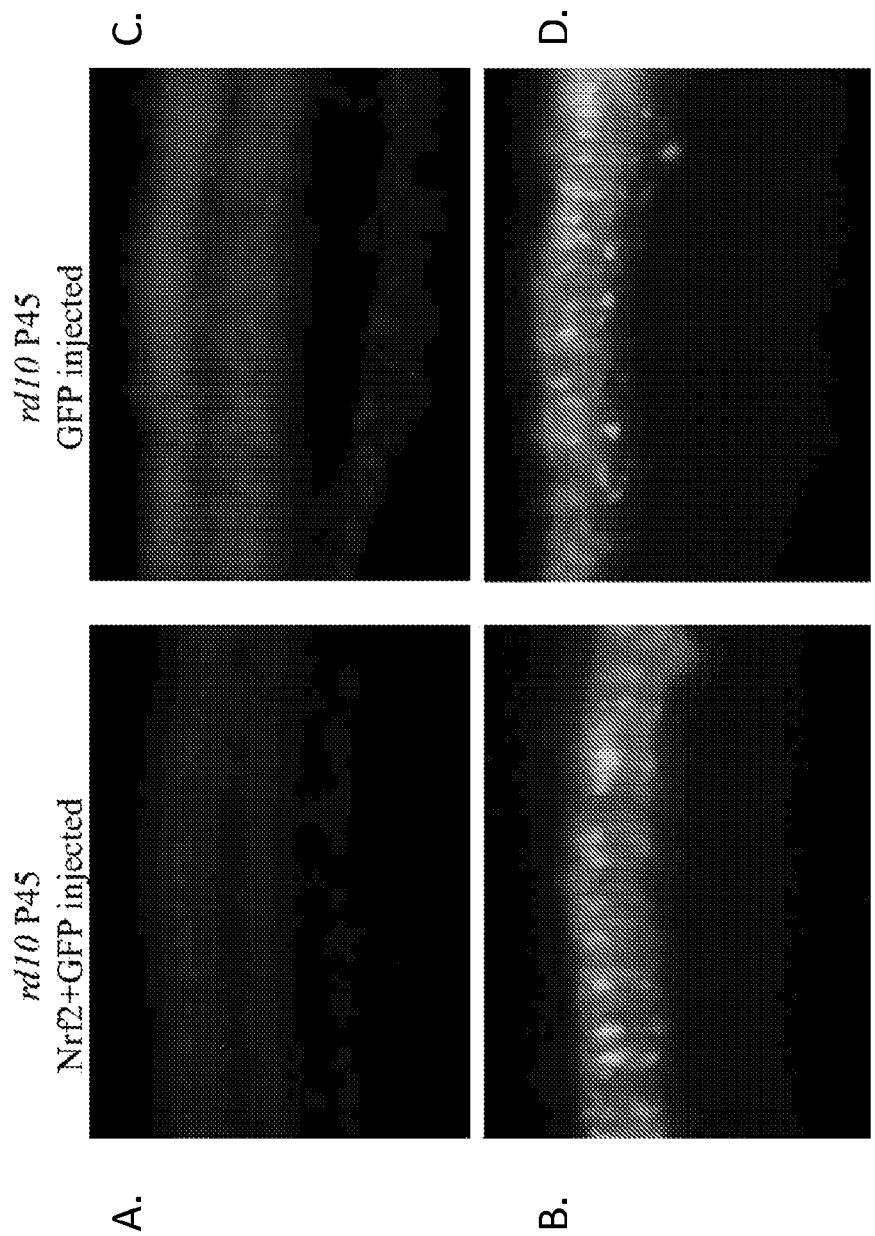

FIG. 20 is a graph demonstrating that overexpression of Nrf2 preserves cone outer segments. The phenotype was quantified by counting the percentage of cones with PNA staining. The mid dorsal regions of the P50 retinas were chosen for quantification. Numbers are shown as mean±SEM.

FIGS. 21A-21D are photomicrographs demonstrating that treatment of Nrf2 reduces superoxide levels. Hydroethidine (DHE) was injected intraperitoneally at postnatal day (P) 45 into rd10 mice treated with AAV-CMV-GFP or rd10 mice treated with AAV-CMV-GFP+AAV-CMV-Nrf2. After 18 hours, mice were euthanized and retinas were harvested. Stronger fluorescence in AAV-CMV-GFP injected retinas (C) demonstrates higher level of superoxide species produced. Minimal fluorescence was present in the retinas treated with AAV-CMV-GFP+AAV-CMV-Nrf2 (A). B and D show the GFP green fluorescence of the retinas in A and C.

FIGS. 22A-22F are photomicrographs demonstrating that overexpression of Nrf2 reduces lipid oxidation in cones. P30 rd1 retinas were harvested and immunostained against acrolein-modified proteins. Acrolein is a metabolite of lipid peroxidation and can react with proteins. Retinas infected with AAV-CMV-GFP+AAV-CMV-Nrf2 (D-F) have reduced level of anti-acrolein staining, demonstrating lower levels of lipid oxidation, compared to the control retinas infected with AAV-CMV-GFP (A-C).

FIGS. 23A-23B are graphs demonstrating that overexpression of Nrf2 provides for better visual acuity as shown by the optomotor assay. The right eye of rd10 mice received AAV vector injection, while the left eye was uninjected and served as within-animal control. The right and left eyes of P50 rd10 mice were tested separately, and the visual acuities are shown in (A). The mean visual acuity (±SEM) of the right eyes which received AAV-CMV-GFP+AAV-CMV-Nrf2 treatment is higher than that of the right eyes which received AAV-CMV-GFP treatment. The ratio of Right eye/Left eye visual acuity of each animal was used to minimize the variation between animals without treatment. The R/L ratio of AAV-CMV-GFP+AAV-CMV-Nrf2 treated retinas was significantly higher than that of AAV-CMV-GFP treated retinas (p<0.05) (B).

FIGS. 24A-24C demonstrate that overexpression of Nrf2 results in better visual function as assessed by photopic electroretinography (ERG). P40 rd10 mice were tested for cone-initiated electrical signal by photopic ERG. Representative waveforms are shown in (A-B). The right eye of an AAV-CMG-GFP+AAV-CMV-Nrf2 treated mouse had a substantially better waveform. The ratio of right eye/left eye b-wave amplitude was significantly higher in AAV-CMV-GFP+AAV-CMV-Nrf2 treated mice than that in the control mice (C).

Figure 25:
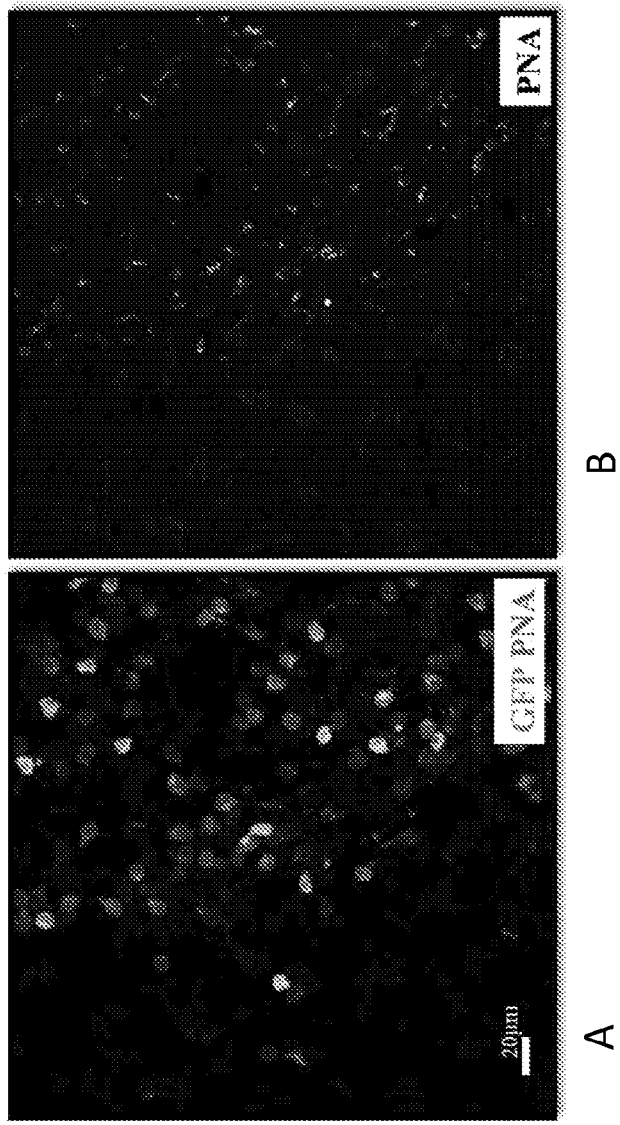

FIGS. 25A-25B demonstrate that overexpression of SOD2 and Catalase preserves outer segments of cones in retinas of rhodopsin null mice (rho−/−). The retinas of rho−/− mice at 6 months of age were infected with AAV vectors expressing SOD2 and Catalase. Retinas were stained with anti PNA to show cone outer segments (OS). A shows PNA and GFP staining. B shows PNA staining.

FIGS. 26A and 26B are graphs depicting the effect of increased expression of Nrf2 and Sod2 on retinal ganglion cell survival (A) and axon regeneration (B) following optic nerve crush in wild-type mice.

DETAILED DESCRIPTION OF THE INVENTION

The present invention is based, at least in part, on the discovery that increased expression and/or activity of genes encoding antioxidant defense protein(s), in a photoreceptor cell undergoing oxidative stress, can inhibit oxidative stress in the affected cell. As rods are the major cell type in the outer nuclear layer (ONL), cones experience a greatly altered environment following rod death. The cone outer segment (OS) collapses, they lose their intimate association with the retinal pigmented epithelium (RPE), and are, thus, exposed to a hyperoxic environment as evidenced by greater oxidation of their nucleic acids, proteins, and lipids. Thus, it has been discovered that cone cells in a mouse model of RP show signs of oxidation. Accordingly, increased expression and/or activity of an antioxidant defense protein, including antioxidant enzymes and transcription factors that generally up-regulate the anti-oxidation program can serve to inhibit cellular oxidative stress, thus, increasing photoreceptor viability. Accordingly, the present invention provides methods for inhibiting oxidative stress of a photoreceptor, as well as methods for the treatment and/or prevention of disorders associated with cellular oxidative stress, for example, retinitis pigmentosa, by increasing the expression and/or activity of at least one antioxidant defense protein.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, the terms "inhibit oxidative stress" and "inhibition of oxidative stress" refer to preventing as well as ameliorating, decreasing, or reducing oxidative stress.

As used herein, the term "antioxidant defense protein" includes any protein that inhibits the oxidation of a molecule. More specifically, an "antioxidant defense protein" encompasses any upstream element (e.g., transcription factor) involved in the anti-oxidation program, as well as any downstream element (e.g., antioxidant enzymes) that can be activated as a result of the enhancement of an upstream element. Exemplary antioxidant defense proteins include, superoxide dismutase 2 (SOD2), catalase, peroxisome proliferator-activated receptor gamma coactivator 1-alpha (PGC1α), and nuclear factor erythroid 2-like 2 (Nrf2).

As used herein, the term "oxidative stress" refers to any imbalance in the normal reduction-oxidation state in a photoreceptor cell that leads to an increase in the level of reactive oxygen species (ROS) resulting in cellular damage including, for example, DNA damage, lipid peroxidation, and oxidation of proteins.

As used herein, the terms "antioxidant enzyme" and "enzymatic scavenger" are used interchangeably to refer to antioxidant proteins capable of detoxifying or ameliorating free radicals, i.e., reactive oxygen species (ROS). Examples include, but are not limited to, alpha-1-microglobulin, superoxide dismutases, catalases, lactoperoxidases, glutathione peroxidases, and peroxiredoxins.

As used herein, the term "reduces the level of ROS" refers to decreasing the level of ROS to physiologically acceptable non-toxic levels, as well as preventing the further generation of ROS.

In one embodiment of the invention, cells suitable for use in the instant methods are photoreceptor cells, i.e., a specialized cell found in the retina. The retina is a thin, transparent tissue containing about 120 million separate rod cells (night vision) and 7 million cone cells (day and color vision) as well as millions of other structural supporting and interconnecting cells. Photoreceptor cells consist of "rods" and "cones", which are the photosensitive cells of the retina. The rods contain rhodopsin, the rod photopigment, and the cones contain other distinct photopigments, which respond to light and ultimately trigger a neural discharge in the output cells of the retina, the ganglion cells. Ultimately, this signal is registered as a visual stimulus in the visual cortex and other target locations in the brain. The retinal pigment epithelial (RPE) cells produce, store and transport a variety of factors that are responsible for the normal function and survival of photoreceptors. Retinal cells that can also sense light consist of photosensitive ganglion cells. These cells, known as the melanopsin ganglion cells are found in the inner retina, have dendrites and long axons projecting to the protectum (midbrain), the suprachiasmatic nucleus in the hypothalamus, and the lateral geniculate (thalamus). In one embodiment, a photoreceptor cell is a rod. In some embodiments, a photoreceptor cell is distinct from the optic nerve. In one embodiment, a photoreceptor cell is a cone. In one embodiment, a photosensitive cell is a cell is a melanopsin ganglion cell.

As used herein, the term "retinal disorder" refers generally to a disorder of the retina. In one embodiment, the retinal disorder is associated with oxidative stress, decreased viability, for example, death, of cone cells, and/or rod cells. Moreover, in a particular embodiment, a retinal disorder is not associated with blood vessel leakage and/or growth, for example, as is the case with diabetic retinopathy, but, instead is characterized primarily by reduced viability of cone cells and/or rod cells. In certain embodiments, the retinal disorder is a genetic disorder. In a particular embodiment, the retinal disorder is retinitis pigmentosa. In another embodiment, the retinal disorder is age-related macular degeneration. In another embodiment, the retinal disorder is cone-rod dystrophy. In another embodiment, the retinal disorder is rod-cone dystrophy. In other embodiments, the retinal disorder is not associated with blood vessel leakage and/or growth. In certain embodiments, the retinal disorder is not associated with diabetes and/or diabetic retinopathy. In further embodiments, the retinal disorder is not NARP (neuropathy, ataxia, and retinitis pigmentosa). In yet further embodiments, the retinal disorder is not a neurological disorder. In certain embodiments, the retinal disorder is not a disorder that is associated with a compromised optic nerve and/or disorders of the brain. In the foregoing embodiments, the retinal disorder is associated with a compromised photoreceptor cell, and is not a neurological disorder.

As used herein, the term "retinitis pigmentosa" or "RP" is known in the art and encompasses a disparate group of genetic disorders of rods and cones. Retinitis pigmentosa generally refers to retinal degeneration often characterized by the following manifestations: night blindness, progressive loss of peripheral vision, eventually leading to total blindness; ophthalmoscopic changes consist in dark mosaic-like retinal pigmentation, attenuation of the retinal vessels, waxy pallor of the optic disc, and in the advanced forms, macular degeneration. In some cases there can be a lack of pigmentation. Retinitis pigmentosa can be associated to degenerative opacity of the vitreous body, and cataract. Family history is prominent in retinitis pigmentosa; the pattern of inheritance may be autosomal recessive, autosomal dominant, or X-linked; the autosomal recessive form is the most common and can occur sporadically.

As used herein, the terms "Cone-Rod Dystrophy" or "CRD" and "Rod-Cone Dystrophy" or "RCD" refer to art recognized inherited progressive diseases that cause deterioration of the cone and rod photoreceptor cells and often result in blindness. CRD is characterized by reduced viability or death of cone cells followed by reduced viability or death of rod cells. By contrast, RCD is characterized by reduced viability or death of rod cells followed by reduced viability or death of cone cells.

As used herein, the term "age-related macular degeneration" also referred to as "macular degeneration" or "AMD", refers to the art recognized pathological condition which causes blindness amongst elderly individuals. Age related macular degeneration includes both wet and dry forms of ARMD. The dry form of ARMD, which accounts for about 90 percent of all cases, is also known as atrophic, nonexudative, or drusenoid (age-related) macular degeneration. With the dry form of ARMD, drusen typically accumulate in the retinal pigment epithelium (RPE) tissue beneath/within the Bruch's membrane. Vision loss can then occur when drusen interfere with the function of photoreceptors in the macula. The dry form of ARMD results in the gradual loss of vision over many years. The dry form of ARMD can lead to the wet form of ARMD. The wet form of ARMD, also known as exudative or neovascular (age-related) macular degeneration, can progress rapidly and cause severe damage to central vision. The macular dystrophies include Stargardt Disease, also known as Stargardt Macular Dystrophy or Fundus Flavimaculatus, which is the most frequently encountered juvenile onset form of macular dystrophy.

As used herein, the term "neurological disorder" encompasses neurodegenerative disorders and demyelinating disorders. In some embodiments, the compositions of this invention are useful for the treatment of neurological disorders including but not limited to Parkinson's Disease, Tauopathies, Alzheimer's Disease, Diffuse Neurofibrillary Tangles with Calcification, Supranuclear Palsy, Progressive, TDP-43 Proteinopathies, Amyotrophic Lateral Sclerosis, Multiple Sclerosis, Frontotemporai Lobar Degeneration, Lewy Body Disease, AIDS Dementia Complex, Aphasia, Primary Progressive, Primary Progressive Nonfluent Aphasia, Dementia, Vascular, CADASIL, Dementia, Multi-Infarct, Diffuse Neurofibrillary Tangles with Calcification, Frontotemporai Lobar Degeneration, Frontotemporai Dementia, Primary Progressive Nonfluent Aphasia, Kluver-Bucy Syndrome, Pick's Disease, Motor Neuron Disease, Bulbar Palsy, Progressive, Muscular Atrophy, Spinal, Multiple System Atrophy, Olivopontocerebellar Atrophies, Shy-Drager Syndrome, Striatonigrai Degeneration, Olivopontocerebellar Atrophies, Paraneoplastic Syndromes, Nervous System, Lambert-Eaton Myasthenic Syndrome, Limbic Encephalitis, Myelitis, Transverse, Opsoclonus-Myoclonus Syndrome, Paraneoplastic Cerebellar Degeneration, Paraneoplastic Polyneuropathy, Postpoliomyelitis Syndrome, Prion Diseases, Encephalopathy, Bovine Spongiform, Gerstmann-Straussler-Scheinker Disease, Insomnia, Fatal Familial, Kuru, Scrapie, Wasting Disease, Chronic, Creutzfeidt-Jakob Syndrome, Shy-Drager Syndrome, Subacute Combined Degeneration, Heredodegenerative Disorders, Nervous System, Alexander Disease, Amyloid Neuropathies, Familial, Bulbo-Spinal Atrophy, X-Linked, Canavan Disease, Cockayne Syndrome, Dystonia Musculorum Deformans, Gerstmann-Straussier-Scheinker Disease, Hepatolenticular Degeneration, Hereditary Central Nervous System Demyelinating Diseases, Hereditary Sensory and Autonomic Neuropathies, Hereditary Sensory and Motor Neuropathy, Huntington Disease, Lafora Disease, Lesch-Nyhan Syndrome, Menkes Kinky Hair Syndrome, Myotonia Congenita, Myotonic Dystrophy, Neurofibromatoses, Neuronal Ceroid-Lipofuscinoses, Optic Atrophies, Hereditary, Pantothenate Kinase-Associated Neurodegeneration, Rett Syndrome, Spinal Muscular Atrophies of Childhood, Spinocerebellar Degenerations, Tourette Syndrome, Tuberous Sclerosis, Unverricht-Lundborg Syndrome, and the similar, and for the treatment of Alzheimer's Disease and associated dementias. In one embodiment, the neurological disease is not Parkinson's Disease.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleic acid molecule used in the methods of the present invention can be isolated using standard molecular biology techniques. Using all or portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques. Furthermore, oligonucleotides corresponding to nucleotide sequences of interest can be prepared by standard synthetic techniques, e.g., using an automated DNA synthesizer.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a nucleic acid molecule of the invention is an siRNA molecule. In another embodiment, a nucleic acid molecule of the invention is an shRNA molecule. In one embodiment, a nucleic acid molecule of the invention mediates RNAi.

In another embodiment, a nucleic acid molecule of the invention mediates translational inhibition. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287. 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F.2003. Mol Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g., New England Biolabs or Ambion. In one embodiment one or more of the chemistries described herein for use in antisense RNA can be employed in molecules that mediate RNAi.

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes or nucleic acid molecules to which they are operatively linked and are referred to as "expression vectors" or "recombinant expression vectors" or simply "expression vectors". Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In some embodiments, "expression vectors" are used in order to permit pseudotyping of the viral envelope proteins.

Expression vectors are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses, adeno-associated viruses, lentiviruses), which serve equivalent functions.

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." LTRs contain numerous regulatory signals, including transcriptional control elements, polyadenylation signals, and sequences needed for replication and integration of the viral genome. LTRs may be several hundred base pairs in length.

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) *Curr. Topics Microbiol. Immunol.* 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) *J. Virology* 76(5): 2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The terms "transformation," "transfection," and "transduction" refer to introduction of a nucleic acid, e.g., a viral vector, into a recipient cell.

As used herein, the term "subject" includes warm-blooded animals, preferably mammals, including humans. In a preferred embodiment, the subject is a primate. In an even more preferred embodiment, the primate is a human.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (i.e., contacting a cell with an agent) is intended to include incubating the agent and the cell together in vitro (e.g., adding the agent to cells in culture) or administering the agent to a subject such that the agent and cells of the subject are contacted in vivo. The term "contacting" is not intended to include exposure of cells to an agent that may occur naturally in a subject (i.e., exposure that may occur as a result of a natural physiological process).

As used herein, the term "administering" to a subject includes dispensing, delivering or applying a composition of the invention, e.g., capable of inhibiting oxidative stress, to a subject by any suitable route for delivery of the composition to the desired location in the subject, including delivery by intraocular administration or intravenous administration. Alternatively or in combination, delivery is by the topical, parenteral or oral route, intracerebral injection, intramuscular injection, subcutaneous/intradermal injection, intravenous injection, buccal administration, transdermal delivery and administration by the rectal, colonic, vaginal, intranasal or respiratory tract route.

Various additional aspects of the methods of the invention are described in further detail in the following subsections.

Methods of the Invention

The present invention provides methods for inhibiting oxidative stress of a photoreceptor cell, which generally comprise contacting a photoreceptor cell with an agent which increases the expression and/or activity of an antioxidant defense protein.

The present invention also provides methods for treating or preventing a retinal disorder, e.g., a retinal disorder associated with oxidative stress of a photoreceptor cell, in a subject. The methods generally comprise administering to the subject an agent which increases the expression and/or activity of an antioxidant defense protein.

In another aspect, the present invention provides methods for treating or preventing retinitis pigmentosa in a subject. Such methods generally comprise administering to the subject an agent which increases the expression and/or activity of an antioxidant defense protein.

The present invention further provides methods for prolonging the viability of a photoreceptor cell, e.g., a photoreceptor cell compromised by a disorder associated with oxidative stress. The methods generally comprise contacting the cell with an agent which increases the expression and/or activity of an antioxidant defense protein.

In the methods of the invention, a cell may be contacted with or a subject administered a single antioxidant defense genes or a combination of antioxidant defense proteins. Suitable antioxidant defense genes include catalase, superoxide dismutase 2 (SOD2), peroxisome proliferator-activated receptor gamma coactivator 1-alpha (PGC1α), nuclear factor erythroid 2-like 2 (nrf2). Suitable combinations of antioxidant defense genes for use in the methods of the invention include catalase; SOD2; PGC1α; nrf2; catalase and SOD2; SOD2 and PGC1α; PGC1α and nrf2; catalase and PGC1α; catalase and nrf2; SOD2 and nrf2; catalase, SOD2, and PGC1α; SOD2, PGC1α, and nrf2; catalase, PGC1α, and nrf2; catalase, SOD2, and nrf2; or catalase, SOD2, PGC1α, and nrf2.

In one embodiment, the methods described herein can be performed in vitro. For example, in on embodiment, intracellular levels of an antioxidant defense protein (e.g., catalase, SOD2, PGC1α, and/or nrf2) can be modulated in a cell in vitro and then the treated cells can be administered or re-administered to a subject. In one embodiment, the cell is a mammalian cell, e.g., a human cell. For practicing the methods in vitro, cells can be obtained from a subject by standard methods and incubated (e.g., cultured) in vitro with an agent which stimulates intracellular levels of an antioxidant defense protein (e.g., catalase, SOD2, PGC1α, and/or nrf2). Methods for isolating cells are well known in the art. The cells can be re-administered to the same subject, or another subject which is compatible with the donor of the cells.

For administration of cells to a subject, it may be preferable to first remove residual agents in the culture from the cells before administering them to the subject. This can be done, for example, by gradient centrifugation of the cells or by washing of the tissue. Methods for the ex vivo genetic modification of cells followed by re-administration to a subject are well known in the art and described in, for example, U.S. Pat. No. 5,399,346 the entire contents of which are incorporated herein by reference.

In one embodiment, the invention provides methods for modulation of intracellular levels of an antioxidant defense protein (e.g., catalase, SOD2, PGC1α, and/or nrf2) in vivo, by administering to a subject a therapeutically effective amount of an agent as described herein. For example, intracellular levels of catalase, SOD2, PGC1α, and/or nrf2 can be modulated to treat or prevent a retinal disorder, such as a retinal disorder associated with cellular oxidative stress of a photoreceptor cells.

The claimed methods of modulation are not meant to include naturally occurring events. For example, the term "agent" or "modulator" is not meant to embrace endogenous mediators produced by the cells of a subject.

Application of the methods of the invention for the treatment and/or prevention of a disorder can result in curing the disorder, decreasing at least one symptom associated with the disorder, either in the long term or short term or simply a transient beneficial effect to the subject. Accordingly, as used herein, the terms "treat," "treatment" and "treating" include the application or administration of agents, as described herein, to a subject who is suffering from a retinal disorder, e.g., associated with oxidative stress of a photoreceptor cell, or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

Subjects suitable for treatment using the regimens of the present invention should have or are susceptible to developing retinal disorders associated with oxidative stress. For example, subjects may be genetically predisposed to development of the disorders. Alternatively, abnormal progression of the following factors including, but not limited to visual acuity, the rate of death of cone and/or rod cells, night vision, peripheral vision, attenuation of the retinal vessels, and other ophthalmoscopic factors associated with retinal disorders such as retinitis pigmentosa may indicate the existence of or a predisposition to a retinal disorder.

The agents, as described herein, may be administered as necessary to achieve the desired effect and depend on a variety of factors including, but not limited to, the severity of the condition, age and history of the subject and the nature of the composition, for example, the identity of the genes or the affected biochemical pathway. In various embodiments, the compositions may be administered at least two, three, four, five or six times a day. Additionally, the therapeutic or preventative regimens may cover a period of at least about 2, 3, 4, 5, 6, 7, 8, 9, 10, 11, 12, 13, 14, 15, 16, 17, 18, 19, 20, 21, 22, 23 or 24 weeks.

The ability of an agent to up-regulate intracellular levels of catalase, SOD2, PGC1α, and/or nrf2 can be determined as described herein, e.g., by determining the ability of the agent to modulate cell viability (e.g., modulation of apoptosis), cleavage of LaminA or Caspase 3; production of reactive oxygen species; assessment for oxidation using immunohistochemical detection of acrolein, as well as ELISA for carbonyl adducts in retinal extracts upon exposure of cells to an oxidant (e.g., paraquat); and/or the expression and protein synthesis of photoreceptor specific opsins.

In various embodiments, the methods of the present invention further comprise monitoring the effectiveness of treatment. For example, visual acuity, the rate of death of cone and/or rod cells, night vision, peripheral vision, attenuation of the retinal vessels, and other ophthalmoscopic changes associated with retinal disorders such as retinitis pigmentosa may be monitored to assess the effectiveness of treatment. Additionally, the rate of death of cells associated with the particular disorder that is the subject of treatment and/or prevention, may be monitored. Alternatively, the viability of such cells may be monitored, for example, as measured by phospholipid production. The assays described in the Examples section below may also be used to monitor the effectiveness of treatment (e.g., electroretinography—ERG).

In one embodiment, an agent for use in the methods of the present invention is a nucleic acid molecule encoding an antioxidant defense protein, e.g., superoxide dismutase 2 (SOD2), catalase, peroxisome proliferator-activated receptor gamma coactivator 1-alpha (PGC1α), and nuclear factor erythroid 2-like 2 (nrf2) (or combinations thereof).

In one embodiment, the nucleic acid molecule encodes superoxide dismutase 2 (SOD2). SOD2 is a member of the iron/manganese superoxide dismutase family. It encodes a mitochondrial protein that forms a homotetramer and binds one manganese ion per subunit. This protein binds to the superoxide byproducts of oxidative phosphorylation and converts them to hydrogen peroxide and diatomic oxygen. There are three alternative transcripts of SOD2, the amino acid sequences of which are known and may be found in, for example, GenBank Accession Nos. GI:67782304, GI:67782306, and GI:67782308.

In another embodiment, the nucleic acid molecule encodes catalase. Catalase is a heme enzyme that is present in the peroxisome of nearly all aerobic cells. Catalase converts the reactive oxygen species hydrogen peroxide to water and oxygen and thereby mitigates the toxic effects of hydrogen peroxide. The amino acid sequence of catalase is known and may be found in, for example, GenBank Accession No. GI: 260436906.

In another embodiment, the nucleic acid molecule encodes peroxisome proliferator-activated receptor gamma coactivator 1-alpha (PGC1α). PGC1α is a transcriptional co-activator that regulates the genes involved in energy metabolism. PGC1α interacts with PPARgamma, which permits the interaction of PGC1α with multiple transcription factors. PGC1α can interact with, and regulate the activities of, cAMP response element binding protein (CREB) and nuclear respiratory factors (NRFs) [Here is correct to keep nuclear respiratory factors]. It provides a direct link between external physiological stimuli and the regulation of mitochondrial biogenesis. The amino acid sequence of PGC1α is known and may be found in, for example, GenBank Accession No. GI:116284374.

In another embodiment, the nucleic acid molecule encodes Nuclear factor (erythroid-derived 2)-like 2 (nrf2), a transcription factor which is a member of a small family of basic leucine zipper (bZIP) proteins. The encoded transcription factor regulates genes which contain antioxidant response elements (ARE) in their promoters. There are three alternative transcripts of nrf2, the amino acid sequences of which are known and may be found in, for example, GenBank Accession Nos. GI:372620347, GI:372620348, and GI:372620346.

In one embodiment, the viability or survival of photoreceptor cells, such as cones cells, is short term viability, e.g., about 1 week, about 2 weeks, about 3 weeks, about 4 weeks, about 5 weeks, about 6 weeks, about 7 weeks, about 8 weeks, about 3 years, about 4 years, about 5 years, about 10 years, about 15, years, about 20 years, about 25 years, about 30 years, about 40 years, about 50 years, about 60 years, about 70 years, and about 80 years.

The methods of the invention described above, thus, may be used to treat or prevent oxidative stress of photoreceptor cells and associated disorders. In one embodiment, the disorder is a retinal disorder including, but not limited to, retinitis pigmentosa, age related macular degeneration, cone rod dystrophy, and rod cone dystrophy. In other embodiments, the retinal disorder is not associated with blood vessel leakage and/or growth. In certain embodiments, the retinal disorder is not associated with diabetes. In another embodiment, the retinal disorder is not diabetic retinopathy. In further embodiments, the retinal disorder is not NARP (neuropathy, ataxia and retinitis pigmentosa). In one embodiment, the disorder is a retinal disorder associated with decreased viability of cone and/or rod cells. In yet another embodiment, the disorder is a genetic disorder.

In one embodiment, the invention is directed to a method of treating or preventing a retinal disorder, such as a retinal disorder associated with oxidative stress of a photoreceptor cell, for example, retinitis pigmentosa, in a subject by selecting a subject who is susceptible to the development of the disorder and administering to the subject an effective amount of the nucleic acid molecules, vectors and/or compositions of the present invention, thereby treating or preventing the disorder in the subject. The overall strategy to save photoreceptor cells from degeneration by exposure to reactive oxygen species as a result of oxidative stress is to supply them with the genes that will allow them to reduce or eliminate the hyperoxic environment by, e.g., inhibiting and/or removing reactive oxygen species by increasing the expression and/or activity of antioxidant defense protein(s).

In general, the nucleic acid molecules and/or the vectors of the invention are provided in a therapeutically effective amount to elicit the desired effect, e.g., inhibit oxidative stress in a photoreceptor cell. The quantity of the nucleic acid molecule, and/or vector to be administered, both according to number of treatments and amount, will also depend on factors such as the clinical status, age, and weight of the subject to be treated, and the severity of the disorder. Precise amounts of active ingredient required to be administered depend on the judgment of the gene therapist and will be particular to each individual patient. For example, a viral vector comprising the nucleic acid molecules of the invention is administered in titers ranging from about $1\times10^5$ to about $1\times10^9$ colony forming units (cfu) per ml, although ranges may vary. Preferred titers will range from about $1\times10^6$ to about $1\times10^8$ cfu/ml.

A therapeutically effective amount of the nucleic acid molecules and/or the vectors of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the nucleic acid molecules and/or the vectors of the invention can include a single treatment or, preferably, can include a series of treatments. It will also be appreciated that the effective dosage used for treatment may increase or decrease over the course of a particular treatment. Changes in dosage may result from the results of diagnostic assays as described herein. The pharmaceutical compositions can be included in a container, pack, or dispenser together with instructions for administration.

The term "prophylactic" or "therapeutic" treatment refers to administration to the subject of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

"Therapeutically effective amount," as used herein, is intended to include the amount of a nucleic acid molecule and/or the vectors of the invention that, when administered to a patient for treating a neurodegenerative disease, is sufficient to effect treatment of the disease (e.g., by diminishing, ameliorating or maintaining the existing disease or one or more symptoms of disease). The "therapeutically effective amount" may vary depending on the nucleic acid molecule, peptide, and/or the vector, how the nucleic acid molecule and/or the vectors is administered, the disease and its severity and the history, age, weight, family history, genetic makeup, stage of pathological processes mediated by the neurodegenerative disease expression, the types of preceding or concomitant treatments, if any, and other individual characteristics of the patient to be treated.

"Prophylactically effective amount," as used herein, is intended to include the amount of a nucleic acid molecule and/or the vector that, when administered to a subject who does not yet experience or display symptoms of e.g., a retinal disorder, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the nucleic acid molecule and/or the vector, how the nucleic acid molecule and/or the vector is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of a nucleic acid molecule and/or the vector that produces some desired local or systemic effect at a reasonable benefit/risk ratio applicable to any treatment. A nucleic acid molecule and/or the vector employed in the methods of the present invention may be administered in a sufficient amount to produce a reasonable benefit/risk ratio applicable to such treatment.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

As used herein, the terms "treating" or "treatment" refer to a beneficial or desired result including, but not limited to, alleviation or amelioration of one or more symptoms, diminishing the extent of infection, stabilized (i.e., not worsening) state of infection, amelioration or palliation of the infectious state, whether detectable or undetectable. "Treatment" can also mean prolonging survival as compared to expected survival in the absence of treatment.

In certain embodiments of the invention, an agent, e.g., an isolated nucleic acid molecule and/or vector of the invention, is administered in combination with an additional therapeutic agent or treatment. The compositions and an additional therapeutic agent can be administered in combination in the same composition or the additional therapeutic agent can be administered as part of a separate composition or by another method described herein.

Examples of additional therapeutic agents suitable for use in the methods of the invention include those agents known to treat retinal disorders, such as retinitis pigmentosa and age-related macular degeneration and include, for example, fat soluble vitamins (e.g., vitamin A, vitamin E, and ascorbic acid), calcium channel blockers (e.g., diltiazem) carbonic anhydrase inhibitors (e.g., acetazolamide and methazolamide), anti-angiogenics (e.g., antiVEGF antibodies), growth factors (e.g., rod-derived cone viability factor (RdCVF), BDNF, CNTF, bFGF, and PEDF), antioxidants, other gene therapy agents (e.g., optogenetic gene therapy, e.g., channelrhodopsin, melanopsin, and halorhodopsin), and compounds that drive photoreceptor regeneration by, e.g., reprogramming Müller cells into photoreceptor progenitors (e.g., alpha-aminoadipate). Exemplary treatments for use in combination with the treatment methods of the present invention include, for example, retinal and/or retinal pigmented epithelium transplantation, stem cell therapies, retinal prostheses, laser photocoagulation, photodynamic therapy, low vision aid implantation, submacular surgery, and retinal translocation.

Agents for Use in the Methods of the Invention

Stimulatory Agents

The methods of the invention may use stimulatory agents which increase the expression and/or activity of an antioxidant defense protein in a cell. Examples of such stimulatory agents include proteins, nucleic acid molecules, e.g., expression vectors comprising nucleic acid molecules, and chemical agents that stimulate expression and/or activity of a protein which increases the expression and/or activity of an antioxidant defense protein in a cell.

A preferred stimulatory agent is a nucleic acid molecule encoding a protein of interest. For example, a cDNA (full length or partial cDNA sequence) is cloned into a recombinant expression vector and the vector is transfected into cells using standard molecular biology techniques. The cDNA can be obtained, for example, by amplification using the polymerase chain reaction (PCR) or by screening an appropriate cDNA library.

Following isolation or amplification of a cDNA, the DNA fragment is introduced into a suitable expression vector. For example, nucleic acid molecules encoding a protein of interest in the form suitable for expression of the protein in a host cell, can be prepared using nucleotide sequences based on the nucleic acid sequence of a nucleic acid molecule encoding the protein of interest.

In one embodiment, a stimulatory agent can be present in an inducible construct. In another embodiment, a stimulatory agent can be present in a construct which leads to constitutive expression.

In one embodiment, the nucleic acid molecules of the invention may be delivered to cells, e.g., photoreceptor cells, or to subjects, in a vector, e.g., a recombinant expression vector. In another embodiment, the nucleic acid molecules of the invention may be delivered to cells, e.g., photoreceptor cells, or to subjects, in the absence of a vector.

As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells, those which are constitutively active, those which are inducible, and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or portions thereof, including fusion proteins or portions thereof, encoded by nucleic acids as described herein.

In one embodiment, a nucleic acid molecule encoding an antioxidant defense protein is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements.

In certain embodiments, the nucleic acid molecules of the invention are contained within a viral vector and may be delivered to cells, e.g., photoreceptor cells, or to subjects. Preferably a viral vector is one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., *Clin. Exp. Immunol.* 107(Suppl. 1):31-32 (1997), as well as Nakanishi, M., *Crit. Rev. Therapeu. Drug Carrier Systems* 12:263-310 (1995); Robbins, P. D., et al., *Trends Biotechnol.* 16:35-40 (1998); Zhang, J., et al., *Cancer Metastasis Rev.* 15:385-401(1996); and Kramm, C. M., et al., *Brain Pathology* 5:345-381 (1995). Such vectors may be derived from viruses that contain RNA (Vile, R. G., et al., *Br. Med Bull.* 51:12-30 (1995)) or DNA (Ali M., et al., *Gene Ther.* 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., *Nat. Med.* 3:639-645 (1997)); adenoviral/retroviral chimeras (Bilbao, G., et al., *FASEB J.* 11:624-634 (1997); Feng, M., et al., *Nat. Biotechnol.* 15:866-870 (1997)); adeno-associated viruses (Flotte, T. R. and Carter, B. J., *Gene Ther.* 2:357-362 (1995); U.S. Pat. No. 5,756,283); herpes simplex virus I or II (Latchman, D. S., *Mol. Biotechnol.* 2:179-195 (1994); U.S. Pat. No. 5,763,217; Chase, M., et al., *Nature Biotechnol.* 16:444-448 (1998)); parvovirus (Shaughnessy, E., et al., *Semin Oncol.* 23:159-171 (1996)); reticuloendotheliosis virus (Donburg, R., *Gene Therap.* 2:301-310 (1995)). Extrachromosomal replicating vectors may also be used in the gene therapy methods of the present invention. Such vectors are described in, for example, Calos, M. P. (1996) *Trends Genet.* 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) *Crit. Rev. Therapeu. Drug Carrier Systems* 12:263-310; Zhang, J., et al. (1996) *Cancer Metastasis Rev.* 15:385-401; Jacoby, D. R., et al. (1997) *Gene Therapy* 4:1281-1283).

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." LTRs contain numerous regulatory signals, including transcriptional control elements, polyadenylation signals, and sequences needed for replication and integration of the viral genome. LTRs may be several hundred base pairs in length.

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) *Curr. Topics Microbiol. Immunol.* 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) *J. Virology* 76(5): 2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

As used herein, the term "adenovirus" ("Ad") refers to a group of double-stranded DNA viruses with a linear genome of about 36 kb. See, e.g., Berkner et al., *Curr. Top. Microbiol. Immunol.*, 158: 39-61 (1992). In some embodiments, the adenovirus-based vector is an Ad-2 or Ad-5 based vector. See, e.g., Muzyczka, *Curr. Top. Microbiol. Immunol.*, 158: 97-123, 1992; Ali et al., 1994 *Gene Therapy* 1: 367-384; U.S. Pat. Nos. 4,797,368, and 5,399,346. Suitable adenovirus vectors derived from the adenovirus strain Ad type 5 d1324 or other strains of adenovirus (e.g., Ad2, Ad3, Ad7, etc.) are well known to those skilled in the art. Recombinant adenoviruses are advantageous in that they do not require dividing cells to be effective gene delivery vehicles and can be used to infect a wide variety of cell types. Additionally, introduced adenovirus DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenovirus genome for foreign DNA is large (up to 8 kilobases) relative to other gene delivery vectors (Haj-Ahmand et al. *J. Virol.* 57, 267-273 [1986]).

In one embodiment, an adenovirus is a replication defective adenovirus. Most replication-defective adenoviral vectors currently in use have all or parts of the viral E1 and E3 genes deleted but retain as much as 80% of the adenovirus genetic material. Adenovirus vectors deleted for all viral coding regions are also described by Kochanek et al. and Chamberlain et al. (U.S. Pat. Nos. 5,985,846 and 6,083,750). Such viruses are unable to replicate as viruses in the absence of viral products provided by a second virus, referred to as a "helper" virus.

In one embodiment, an adenoviral vector is a "gutless" vector. Such vectors contain a minimal amount of adenovirus DNA and are incapable of expressing any adenovirus antigens (hence the term "gutless"). The gutless replication defective Ad vectors provide the significant advantage of accommodating large inserts of foreign DNA while completely eliminating the problem of expressing adenoviral genes that result in an immunological response to viral proteins when a gutless replication defective Ad vector is used in gene therapy. Methods for producing gutless replication defective Ad vectors have been described, for example, in U.S. Pat. No. 5,981,225 to Kochanek et al., and U.S. Pat. Nos. 6,063,622 and 6,451,596 to Chamberlain et al; Parks et al., *PNAS* 93:13565 (1996) and Lieber et al., *J. Virol.* 70:8944-8960 (1996).

In another embodiment, an adenoviral vector is a "conditionally replicative adenovirus" ("CRAds"). CRAds are genetically modified to preferentially replicate in specific cells by either (i) replacing viral promoters with tissue specific promoters or (ii) deletion of viral genes important for replication that are compensated for by the target cells only. The skilled artisan would be able to identify epithelial cell specific promoters.

Other art known adenoviral vectors may be used in the methods of the invention. Examples include Ad vectors with recombinant fiber proteins for modified tropism (as described in, e.g., van Beusechem et al., 2000 *Gene Ther.* 7: 1940-1946), protease pre-treated viral vectors (as described in, e.g., Kuriyama et al., 2000 *Hum. Gene Ther.* 11: 2219-2230), E2a temperature sensitive mutant Ad vectors (as described in, e.g., Engelhardt et al., 1994 *Hum. Gene Ther.* 5: 1217-1229), and "gutless" Ad vectors (as described in, e.g., Armentano et al., 1997 *J. Virol.* 71: 2408-2416; Chen et al., 1997 *Proc. Nat. Acad. Sci. USA* 94: 1645-1650; Schieder et al., 1998 *Nature Genetics* 18: 180-183).

In a particular embodiment, the viral vector for use in the methods of the present invention is an AAV vector. In particular embodiments, the viral vector is an AAV2/5 or AAV2/8 vector. Such vectors are described in, for example, U.S. Pat. No. 7,056,502, the entire contents of which are incorporated herein by reference. In another embodiment, adenoviral vectors suitable for use in the present invention may include those that are capable of transducing all retinal cell types upon intravitreal administration, such as an AAV2 variant having a V7081 mutation. Additional suitable adenoviral vectors are those that do not generate a humoral immune response against the viral capsid upon administration (see, e.g., Dalkara et al, 2013 *Sci Transl Med.* 5, 189ra76), and those that facilitate nuclear transport of the AAV vector by, e.g., reducing ubiquitination and proteasome-mediated degradation of the vector, such as vectors having mutations that prevent phosphorylation of tyrosine residues in AAV capsid proteins (as described in e.g., Pang et al, 2010 *The American Society of Gene & Cell Therapy.* 19, 2: 234-242).

The vector will include one or more promoters or enhancers, the selection of which will be known to those skilled in the art. For example, commonly used promoters are derived from polyoma, adenovirus 2, cytomegalovirus and simian virus 40.Suitable promoters include, but are not limited to, the retroviral long terminal repeat (LTR), the SV40 promoter, the human cytomegalovirus (CMV) promoter, and other viral and eukaryotic cellular promoters known to the skilled artisan. For other suitable expression systems for both prokaryotic and eukaryotic cells see chapters 16 and 17 of Sambrook, J., Fritsh, E. F., and Maniatis, *T. Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the viral vector is capable of directing expression of the nucleic acid preferentially in a particular cell type (e.g., tissue-specific regulatory elements are used to express the nucleic acid). Tissue-specific regulatory elements are known in the art. In one embodiment, a tissue-specific promoter for use in the vectors and methods of the invention is a retinal cell-specific promoter. In one embodiment, a retinal cell-specific promoter is a rod-, cone-, and bipolar cell-specific promoter. In one embodiment, a retinal cell-specific promoter is a rod- and cone-specific promoter. In one embodiment, a retinal cell-specific promoter is a rod-specific promoter. In one embodiment, a retinal cell-specific promoter is a cone-specific promoter.

Suitable retinal cell-specific promoters are known in the art and include, e.g., rhodopsin regulatory sequences, Nrl, Crx, Rax, and the like (Matsuda and Cepko (2007) *Proc. Natl. Acad. Sci. U.S.A.* 104:1027), opsin promoters, e.g., cone opsin, interphotoreceptor retinoid binding protein promoters (IRBP156), rhodopsin kinase (RK) promoters, neural leucine zipper (NRLL) promoters, (see, e.g., Semple-Rowland, et al. (2010) *Molec Vision* 16:916), or combinations thereof. Additional suitable promoters may include cone arrestin, Cabp5, Cralbp, Ndrg4, clusterin, Hes1, vimentin promoters, cluster differentiation (CD44) promoters, and glial fibrillary acid protein (GFAP) promoters.

Guidance in the construction of gene therapy vectors and the introduction thereof into affected animals for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for transfection and transformation of the cells of interest. For example, a virus can be placed in contact with the neuronal cell of interest or alternatively, can be injected into a subject suffering from a neurodegenerative disorder.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

As discussed above, the nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470), stereotactic injection (see, e.g., Chen et al. (1994) *Proc. Natl. Acad. Sci. U.S.A.* 91:3054), or by in vivo electroporation (see, e.g., Matsuda and Cepko (2007) *Proc. Natl. Acad. Sci. U.S.A.* 104:1027). Local administration of nucleic acids and/or gene therapy vectors described herein can be by any suitable method in the art including, for example, injection (e.g., intravitreal or subretinal or subvitreal injection), gene gun, by topical application of the nucleic acid in a gel, oil, or cream, by electroporation, using lipid-based transfection reagents, transcleral delivery, by implantation of scleral plugs or a drug delivery device, or by any other suitable transfection method.

In one embodiment, a packaging cell line is transduced with a retroviral vector carrying the desired nucleic acid molecule to form a producer cell line. The packaging cells may be transduced by any means known in the art, including, e.g., electroporation, CaPO$_4$ precipitation, or the use of liposomes. Examples of packaging cells that may be transfected include, but are not limited to, BOSC23, Bing, PE501, PA317, .PSI.-2, .PSI.-AM, PA12, T19-14X, VT-19-17-H2, .PSI.-CRE, .PSI.-CRIP, GP+E86, GP+envAm12, and DAN cell lines. Guidance on retroviral producing packaging cells and how to construct them can be found in Short et al., *J. Neurosci. Res.* 27:427-433 (1990); Miller, A. D., *Human Gene Ther.* 1:5-14 (1990); Danos, O, "Construction of Retroviral Packaging Cell Lines," in Methods in Molecular Biology (M. Collins, ed.), Vol. 8, The Humana Press Inc., Clifton, N.J., 17-26 (1991); Murdoch, B., et al., *Gene Therapy* 4:744-749 (1997); and U.S. Pat. Nos. 5,529,774 and 5,591,624, the entire contents of which are incorporated herein by reference.

Retroviral vectors have may also be packaged with a vesicular stomatitis virus (VSV) envelope glycoprotein G ("pseudotyping"). These vectors are more stable and can be concentrated to $10^9$ cfu/ml, allowing them to be injected directly (Burns, J. C. et al. (1993) *Proc. Natl. Acad. Sci. USA* 90:8033-8037).

The producer cells can then be grafted near or into the desired location, for example, intraocularly. Direct injection of high titer retroviral producer cells (Murdoch, B., et al., *Gene Ther.* 4:744-749 (1997); Onodera, M., et al., *Hum Gene Ther.* 8:1189-1194 (1997)) allow for efficient in situ infection with the retroviral sequences (Rainov, N. G., et al., *Cancer Gene Ther.* 3:99-106 (1996); Ram, Z., et al., *Cancer Res.* 53:83-88 (1993)). Producer cells injected intraocularly do not generally migrate from the site of injection. Moreover, although they may be rejected by the host, this does not occur for 5-10 days, by which time retroviral infection of nearby cells will have occurred (Ram, Z., et al., *J. Neurosurg.* 79:400-407 (1993)). In general, vector producer cell (VPC) dosages range from about $2.5\times10^8$, about $1\times10^8$, about $1.5\times10^8$, about $2\times10^8$, about $2.5\times10^8$, about $3\times10^8$, about $3.5\times10^8$, about $4\times10^8$, about $4.5\times10^8$, about $5\times10^8$, about $5.5\times10^8$, about $6\times10^8$, about $6.5\times10^8$, about $7\times10^8$, about $7.5\times10^8$, about $8\times10^8$, about $8.5\times10^8$, about $9\times10^8$, about $9.5\times10^8$, and about $1\times10^9$ VPCs. The exact amount of producer cells will ultimately be determined by the skilled artisan based on numerous factors, including, but not limited to, the available injectable volume, clinical status of the patient, and the severity of the disorder.

The exact amount of producer cells will ultimately be determined by the skilled artisan based on numerous factors, including, but not limited to, the available injectable volume, clinical status of the patient, and the severity of the disorder.

Preferably, the viral genomes of the viral vectors used in the invention should be modified to remove or limit their ability to replicate, however, replication conditional viruses will also be useful in the present invention, as will replicating vectors that are capable of targeting certain cells. (See, e.g., Zhang, J. et al. (1996) *Cancer Metastasis Rev.* 15:385-401).

The nucleic acid molecules can also be delivered using non-viral methods for gene transfer, preferably those whose use in gene therapy is known in the art (Nakanishi, M., *Crit. Rev. Therapeu. Drug Carrier Systems* 12:263-310 (1995); Abdallah, B., et al., *Biol Cell* 85:1-7 (1995); Zhang, J., et al., *Cancer Metastasis Rev.* 15:385-401 (1996); Philips, S. C., *Biologicals* 23:13-16 (1995); Lee, R. J. and Huang, L., *Crit. Rev. Ther. Drug Carrier Syst.* 14:173-206 (1997)). Examples of such non-viral vectors for gene delivery include prokaryotic vectors, cationic liposomes, DNA-protein complexes, non-viral T7 autogene vectors (Chen, X., et al., *Hum. Gene Ther.* 9:729-736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburstpolyamidoamine dendrimers (Kukowska-Latallo, J. F., et al., *Proc Natl Acad Sci USA* 93:4897-4902 (1996); Tang, M. X., et al., *Bioconjug. Chem.* 7:703-714 (1996)), cationic peptides (Wyman, T. B., et al., *Biochemistry* 36:3008-3017 (1997)), and mammalian artificial chromosomes (Ascenzioni, F., et al., *Cancer Lett.* 118:135-142 (1997)).

Any suitable virus usable for nucleic acid delivery may be used, including, but not limited to, adenovirus, adeno-associated virus, retroviruses and the like. For example, the LIA retrovirus may be used to deliver nucleic acids (Cepko et al. (1998) *Curr. Top. Dev. Biol.* 36:51; Dyer and Cepko (2001) *J. Neurosci.* 21:4259).

In one embodiment, a single viral vector is used to carry multiple nucleic acid molecules. In another embodiment, two viral vectors are used each carrying one or more genes of interest. If two viral vectors are used, they can be derived from the same or a different type of virus, and can be administered simultaneously or sequentially (i.e., without regard for a specific order).

Gene delivery can be enhanced by including an internal ribosome entry site (IRES) sequence to achieve coordinate expression of multiple genes on a bicistronic message. IRESs are sequences containing 500-600 bp that are typical of the 5' nontransduced regions of picornaviruses, including the polio- and encephalomyocarditis viruses (EMCV). See, e.g., Ghattas, I. R., et al., Molecular and Cellular Biology 11:5848-5859 (1991); Morgan, R. A., et al., Nucleic Acids Research 20:1293-1299 (1992). This approach has been used for efficient retroviral coexpression of the two subunits of interleukin-12 (Tahara, H., et al., J. Immunol. 154:6466-6474 (1995)). Similarly, a viral sequence, the picornavirus 2A sequence, can be used to create mRNAs encoding more than one protein. The viral 2A peptide is 16-20 amino acids and can be employed as a cleavage peptide located between two proteins of interest, where it promotes their cleavage into two separate proteins (Furler et al. Gene Ther. 8:864-873 (2001). Another alternative is for the vector to contain multiple genes under the control of distinct promoters.

Generally, methods are known in the art for viral infection of the cells of interest. The virus can be placed in contact with the neuronal cell of interest or alternatively, can be injected into a subject suffering from a disorder associated with photoreceptor cell oxidative stress.

In one aspect of the invention, the therapeutic nucleic acid molecule or the vector containing the same will be in the form of a pharmaceutical composition containing a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for intraocular, parenteral, intravenous, intraperitoneal, topical, or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the gene therapy vector, use thereof in the pharmaceutical compositions of the invention is contemplated. Supplementary active compounds can also be incorporated into the compositions.

In a particular embodiment, the pharmaceutical compositions of the present invention would be administered in the form of injectable compositions. The vector can be prepared as an injectable, either as liquid solutions or suspensions. The preparation may also be emulsified. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In a particular embodiment, the nucleic acid molecules and/or vectors are incorporated in a composition suitable for intraocular administration. For example, the compositions may be designed for intravitreal, subconjuctival, sub-tenon, periocular, retrobulbar, suprachoroidal, and/or intrascleral administration, for example, by injection, to effectively treat the retinal disorder. Additionally, a sutured or refillable dome can be placed over the administration site to prevent or to reduce "wash out", leaching and/or diffusion of the active agent in a non-preferred direction.

Relatively high viscosity compositions, as described herein, may be used to provide effective, and preferably substantially long-lasting delivery of the nucleic acid molecules and/or vectors, for example, by injection to the posterior segment of the eye. A viscosity inducing agent can serve to maintain the nucleic acid molecules and/or vectors in a desirable suspension form, thereby preventing deposition of the composition in the bottom surface of the eye. Such compositions can be prepared as described in U.S. Pat. No. 5,292,724, the entire contents of which are hereby incorporated herein by reference.

In general, the nucleic acid molecule is provided in a therapeutically effective amount to elicit the desired effect, e.g., increase the expression and/or activity of an antioxidant defense protein (e.g., catalase, SOD2, PGC1α, and/or nrf2). The quantity of the vector to be administered, both according to number of treatments and amount, will also depend on factors such as the clinical status, age, and weight of the subject to be treated, and the severity of the disorder. Precise amounts of active ingredient required to be administered depend on the judgment of the gene therapist and will be particular to each individual patient. Generally, the viral vector is administered in titers ranging from about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10$, about $9 \times 10^6$, about $9.5 \times 10^6$, about $1 \times 10^7$, about $1.5 \times 10^7$, about $2 \times 10^7$, about $2.5 \times 10^7$, about $3 \times 10^7$, about $3.5 \times 10^7$, about $4 \times 10^7$, about $4.5 \times 10^7$, about $5 \times 10^7$, about $5.5 \times 10^7$, about $6 \times 10^7$, about $6.5 \times 10^7$, about $7 \times 10^7$, about $7.5 \times 10^7$, about $8 \times 10^7$, about $8.5 \times 10^7$, about $9 \times 10^7$, about $9.5 \times 10^7$, about $1 \times 10^8$, about $1.5 \times 10^8$, about $2 \times 10^8$, about $2.5 \times 10^8$, about $3 \times 10^8$, about $3.5 \times 10^8$, about $4 \times 10^8$, about $4.5 \times 10^8$, about $5 \times 10^8$, about $5.5 \times 10^8$, about $6 \times 10^8$, about $6.5 \times 10^8$, about $7 \times 10^8$, about $7.5 \times 10^8$, about $8 \times 10^8$, about $8.5 \times 10^8$, about $9 \times 10^8$, about $9.5 \times 10^8$, and about $1 \times 10^9$ colony forming units (cfu) per ml, although ranges may vary. Preferred titers will range from about $1 \times 10^6$ to about $1 \times 10^8$ cfu/ml.

Other examples of stimulatory agents for increasing the expression and/or activity of an antioxidant defense protein (catalase, SOD2, PGC1α, and/or nrf2) in a cell is a small molecule compound, an antibody, or other protein as described below.

Inhibitory Agents

The methods of the invention may also use agents which inhibit a negative regulator that counteracts the increase in expression and/or activity of an antioxidant defense protein (catalase, SOD2, PGC1α, and/or nrf2). Such agents can be, for example, intracellular binding molecules that act to specifically inhibit the expression, processing, post-translational modification, or activity of a negative regulator that counteracts the increase in expression and/or activity of an antioxidant defense protein (catalase, SOD2, PGC1α, and/or nrf2). As used herein, the term "intracellular binding molecule" is intended to include molecules that act intracellularly to, for example, inhibit the processing expression or activity of a protein by binding to the protein or to a nucleic acid (e.g. an mRNA molecule) that encodes the protein.

Examples of intracellular binding molecules, described in further detail below, include antisense nucleic acids, intracellular antibodies, peptidic compounds, and chemical agents that specifically inhibit the activity of a negative regulator that counteracts the increase in expression and/or activity of an antioxidant defense protein (catalase, SOD2, PGC1α, and/or nrf2).

In one embodiment, such an agent is an antisense nucleic acid molecule that is complementary to a gene encoding a negative regulator that counteracts the increase in expression and/or activity of an antioxidant defense protein (catalase, SOD2, PGC1α, and/or nrf2), or to a portion of the gene, or a recombinant expression vector encoding the antisense nucleic acid molecule. The use of antisense nucleic acids to downregulate the expression of a particular protein in a cell is well known in the art (see e.g. Weintraub, H. et al., Antisense RNA as a molecular tool for genetic analysis, Reviews—Trends in Genetics, Vol. 1(1) 1986; Askari, F. K. and McDonnell, W. M. (1996) N. Eng J. Med. 334:316-318; Bennett, M. R. and Schwartz, S. M. (1995) Circulation 92:1981-1993; Mercola, D. and Cohen, J. S. (1995) Cancer Gene Ther._:47-59; Rossi, J. J. (1995) Br. Med. Bull. 51:217-225; Wagner, R. W. (1994) Nature 372:333-335; each of which is incorporated herein by reference). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule.

Antisense sequences complementary to a sequence of an mRNA can be complementary to a sequence found in the coding region of the mRNA, the 5' or 3' untranslated region of the mRNA or a region bridging the coding region and an untranslated region (e.g. at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g. an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

Antisense nucleic acid molecules are typically administered to a subject or generated in situ such that they hybridize with or bind to cellular mRNA and/or genomic DNA encoding a protein to thereby inhibit expression of the protein, e.g. by inhibiting transcription and/or translation. The hybridization can be by conventional nucleotide complementarily to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g. by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, an antisense nucleic acid molecule that may be used in the methods of the invention is an α-anomeric nucleic acid molecule. An α-anomeric nucleic acid molecule forms specific double-stranded hybrids with complementary RNA in which, contrary to the usual, 8-units, the strands run parallel to each other (Gaultier et al. (1987) Nucleic Acids. Res. 15:6625-6641; incorporated herein by reference). The antisense nucleic acid molecule can also comprise a 2'-o-methylribonucleotide (Inoue et al. (1987) Nucleic Acids Res. 15:6131-6148; incorporated herein by reference) or a chimeric RNA-DNA analogue (Inoue et al. (1987) FEBSLett. 215:327-330; incorporated herein by reference).

In still another embodiment, an antisense nucleic acid molecule that may be used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g. hammerhead ribozymes (described in Haselhoff and Gerlach (1988) Nature 334:585-591; incorporated herein by reference)) can be used to catalytically cleave mRNA transcripts to thereby inhibit translation mRNAs. A ribozyme having specificity for an encoding nucleic acid molecule of interest can be designed based upon the nucleotide sequence of the cDNA. For example, a derivative of a Tetrahynena L-19 WS RNA can be constructed in which the nucleotide sequence of the active site is complementary to the nucleotide sequence to be cleaved in, an encoding mRNA of interest. See, e.g. Cech et al. U.S. Pat. No. 4,987,071; Cech et al. U.S. Pat. No. 5,116,742; each of which is incorporated herein by reference. Alternatively, a mRNA of interest can be used to select a catalytic RNA having a specific ribonuclease activity from a pool of RNA molecules. See, e.g., Bartel, D. and Szostak, J. W. (1993) Science 261:1411-1418; incorporated herein by reference.

In another embodiment, an agent that promotes RNAi can be used to inhibit expression of a negative regulator that counteracts the increase in expression and/or activity of an antioxidant defense protein (catalase, SOD2, PGC1α, and/or nrf2). RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287. 2431-2432 (2000); Zamore et al. Cell 101, 25-33 (2000). Tuschl et al. Genes Dev. 13. 3191-3197 (1999); Cottrell T R, and Doering T L. 2003. Trends Microbiol. 11:37-43; Bushman F.2003. Mol Therapy. 7:9-10; McManus M T and Sharp P A. 2002. Nat. Rev. Genet. 3:737-47; each of which is incorporated herein by reference). The process occurs when an endogenous ribonuclease cleaves the longer dsRNA into shorter, e.g. 21- or 22-nucleotide-long RNAs, termed small interfering RNAs or siRNAs.

The smaller RNA segments then mediate the degradation of the target mRNA. Kits for synthesis of RNAi are commercially available from, e.g New England Biolabsor Ambion. In one embodiment one or more of the chemistries described above for use in antisense RNA can be employed in molecules that mediate RNAi.

Antibodies can also be used as agents in the methods of the invention. In one embodiment, an antibody is an intracellular antibody that inhibits protein activity. Such an intracellular antibody is prepared using methods well known in the art which generally involve preparing a recombinant expression vector which encodes the antibody chains in a form such that, upon introduction of the vector into a cell, the antibody chains are expressed as a functional antibody in an intracellular compartment of the cell.

For inhibition of transcription factor activity according to the inhibitory methods of the invention, an intracellular antibody that specifically binds the protein is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g. Biocca et al. (1990) EMBO J. 9:101-108; Mhashilkar et al. (1995) EMBO J. 14:1542-1551; each of which is incorporated herein by reference). A preferred nuclear localization signal to be used for nuclear targeting of the intracellular antibody chains is the nuclear localization signal of SV40 Large T antigen (see Biocca et al. (1990) EMBO J. 9:101-108; Mhashilkar et al. (1995) EMBO J. 14:1542-1551; each of which is incorporated herein by reference).

To prepare an intracellular antibody expression vector, antibody light and heavy chain cDNAs encoding antibody chains specific for the target protein of interest, is isolated, typically from a hybridoma that secretes a monoclonal antibody specific for the protein. Antibodies can be prepared by immunizing a suitable subject, (e.g. rabbit, goat, mouse or other mammal), e.g., with a protein immunogen. An appropriate immunogenic preparation can contain, for example, recombinantly expressed protein or a chemically synthesized peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, Nature 256:495-497; incorporated herein by reference) (see also, Brown et al. (1981) J. Immunol 127:539-46; Brown et al. (1980) J Biol Chem 255:4980-83; Yeh et al. (1976)PNAS76:2927-31;Yeh et al. (1982) Int. J. Cancer 29:269-75; each of which is incorporated herein by reference). The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet., 3:231-36; each of which is incorporated herein by reference). Briefly, an immortal cell line (typically a myeloma) is fused to lymphocytes (typically splenocytes) from a mammal immunized with a protein immunogen as described above, and the culture supernatants of the resulting hybridoma cells are screened to identify a hybridoma producing a monoclonal antibody that binds specifically, a protein of interest. Any of the many well known protocols used for fusing lymphocytes and immortalized cell lines can be applied for the purpose of generating a monoclonal antibody (see, e.g. G. Galfre et al. (1977) Nature 266:550-52; Gefter et al. Somatic Cell Genet., cited supra; Lerner, Yale J. Biol. Med., cited supra; Kenneth, Monoclonal Antibodies, cited supra; each of which is incorporated herein by reference). Moreover, the ordinary skilled artisan will appreciate that there are many variations of such methods which also would be useful.

Typically, the immortal cell line (e.g. a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the protein are identified by screening the hybridoma culture supernatants for such antibodies, e.g. using a standard ELISA assay.

Alternative to preparing monoclonal antibody-secreting hybridomas, a monoclonal antibody that binds to a protein can be identified and isolated by screening a recombinant combinatorial immunoglobulin library (e.g. an antibody phage display library) with the protein, or a peptide thereof, to thereby isolate immunoglobulin library members that bind specifically to the protein. Kits for generating and screening phage display libraries are commercially available (e.g. the Pharmacia Recombinant Phage Antibody System, Catalog No. 27-9400-01; and the Stratagene SurJZAP™ Phage Display Kit, Catalog No. 240612; each of which is incorporated herein by reference).

Examples of methods and compounds particularly amenable for use in generating and screening antibody display libraries can also be found in, for example, Ladner et al U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; Grifeths et al. (1993) EMBO J 12:725-734; Hawkins et al. (1992) J Mol Biol 226:889-896; Clarkson et al. (1991) Nature 352:624-628; Gram et al. (1992) PNAS 89:3576-3580; Garrad et al. (1991) Bio/Technology 9:1373-1377; Hoogenboom et al. (1991) NucAcid Res 19:4133-4137; Barbas et al. (1991) PNAS 88:7978-7982; McCafferty et al. Nature (1990) 348:552-554; each of which is incorporated herein by reference.

In another embodiment, ribosomal display can be used to replace bacteriophage as the display platform for identifying antibodies for use in the methods of the invention (see, e.g.

Hanes et al. 2000. Nat. Biotechnol. 18:1287; Wilson et al. 2001. Proc. Natl. Acad. Sci. USA 98:3750; Irving et al. 2001 J. Immunol. Methods 248:31; each of which is incorporated herein by reference). In yet another embodiment, cell surface libraries can be screened for antibodies (Boder et al. 2000. Proc. Natl. Acad. Sci. USA 97: 10701; Daugherty et al. 2000 J. Immunol. Methods 243:211; each of which is incorporated herein by reference). Such procedures provide alternatives to traditional hybridoma techniques for the isolation and subsequent cloning of monoclonal antibodies.

In another embodiment, an antibody that may be used in the methods of the invention is a substantially human antibody generated in transgenic animals (e.g., mice) that are incapable of endogenous immunoglobulin production (see e.g. U.S. Pat. Nos. 6,075,181, 5,939,598, 5,591,669 and 5,589,369 each of which is incorporated herein by reference).

For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies can also be isolated and manipulated as described herein.

Yet another highly efficient means for generating recombinant antibodies for use in the methods of the invention is disclosed by Newman, Biotechnology, 10:1455-1460 (1992); incorporated herein by reference. Specifically, this technique results in the generation of primatized antibodies that contain monkey variable domains and human constant sequences. This reference is incorporated by reference in its entirety herein. Moreover, this technique is also described in U.S. Pat. Nos. 5,658,570, 5,693,780 and 5,756,096; each of which is incorporated herein by reference.

Once a monoclonal antibody has been identified (e.g. either a hybridoma-derived monoclonal antibody or a recombinant antibody from a combinatorial library, including monoclonal antibodies that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g. phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) Sequences of Proteins of Immunological Interest, Fifth Edition, U. S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g. from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly.

In another embodiment, an inhibitory agent for use in the methods of the invention is a peptidic compound derived from the amino acid sequence of a negative regulator that counteracts the increase in expression and/or activity of an antioxidant defense protein (catalase, SOD2, PGC1α, and/or nrf2).

Peptidic compounds useful in the method of the invention can be made intracellularly by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g., a GST fusion). Alternative to recombinant synthesis of the peptides in the cells, the peptides can be made by chemical synthesis using standard peptide synthesis techniques.

Synthesized peptides can then be introduced into cells by a variety of means known in the art for introducing peptides into cells (e.g., liposome and the like).

Another form of an inhibitory agent which inhibits a negative regulator that counteracts the increase in expression and/or activity of an antioxidant defense protein (catalase, SOD2, PGC1α, and/or nrf2) in a cell is a chemical small molecule compound.

Pharmaceutical Compositions of the Invention

In one aspect of the invention, a therapeutic nucleic acid molecule and/or vector containing the same will be in the form of a pharmaceutical composition containing a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. In one embodiment, the pharmaceutically acceptable carrier is not phosphate buffered saline (PBS). In one embodiment, the carrier is suitable for intraocular, topical, parenteral, intravenous, intraperitoneal, or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the gene therapy vector, use thereof in the pharmaceutical compositions of the invention is contemplated. Supplementary active compounds can also be incorporated into the compositions.

In a particular embodiment, the pharmaceutical compositions of the present invention would be administered in the form of injectable compositions. The compositions can be prepared as an injectable, either as liquid solutions or suspensions. The preparation may also be emulsified. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In a particular embodiment, the nucleic acid molecules and/or vectors are incorporated in a composition suitable for intraocular administration. For example, the compositions may be designed for intravitreal, subretinal, subconjuctival, sub-tenon, periocular, retrobulbar, suprachoroidal, and/or intrascleral administration, for example, by injection, to effectively treat the retinal disorder. Additionally, a sutured or refillable dome can be placed over the administration site to prevent or to reduce "wash out", leaching and/or diffusion of the active agent in a non-preferred direction.

Relatively high viscosity compositions, as described herein, may be used to provide effective, and preferably substantially long-lasting delivery of the nucleic acid molecules and/or vectors, for example, by injection to the posterior segment of the eye. A viscosity inducing agent can serve to maintain the nucleic acid molecules and/or vectors in a desirable suspension form, thereby preventing deposition of the composition in the bottom surface of the eye. Such compositions can be prepared as described in U.S. Pat. No. 5,292,724, the entire contents of which are hereby incorporated herein by reference.

Sterile injectable solutions can be prepared by incorporating the compositions of the invention in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the compositions of the invention are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compositions of the invention can also be prepared in the form of suppositories (e.g., with conventional suppository bases such as cocoa butter and other glycerides) or retention enemas for rectal delivery.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of nucleic acid molecules described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

This invention is further illustrated by the following examples which should not be construed as limiting. The contents of all references, patents and published patent applications cited throughout this application, as well as the Figures, are hereby incorporated by reference.

EXAMPLES

Materials and Methods
Mouse Strains

Three mouse models of retinitis pigmentosa (RP), rd1, rd10 and rhodopsin knock-out (rho−/−), were chosen for the following studies. The rd1 allele on the FVB/NJ background was chosen since these animals show rapid rod death, followed by relatively rapid cone death, due to homozygosity of the phosphodiesterase 6 beta gene rd1 allele. Compared to rd1, the phenotype of mice carrying the phosphodiesterase 6 beta gene rd10 allele is characterized by a slightly later onset of retinal degeneration. The rd10 mice used in these studies were on a congenic C57BL/6J background and are, thus, suitable for behavioral assays and ERG assays.

A third strain of mice used in these studies carries the rhodopsin rho null allele (rho) which is described by Lem et al. (PNAS 96(2):736-41, 1999). This strain has an intermediate speed of degeneration. In addition, mutation of the rhodopsin gene is the most common mutation found in autosomal RP in humans.

Infection Protocol

Generally, P0 neonates were anesthetized on ice. About 0.3 µl of an AAV virus was introduced into the subretinal space using a pulled glass pipette. Animals were allowed to survive for one week to one year, as several of the animal models for blindness have a slow degeneration. During this time, they were tested for visually guided behavior. Finally, they were euthanized and the histology of their eyes examined.

Figure 7:
FIG. 7 depicts that co-injection with high titer AAV vectors leads to many cells being co-infected. A P0 WT retina was injected with a mixture of two AAV vectors, one encoding GFP (light gray) and one encoding tdTomato (bright light gray). Arrow indicates an example of a double infected cone. Quantification of 200 cells across 2 retinas showed that 100% of cones, identified by PNA staining, were co-infected and 85% of all photoreceptors were co-infected.

Because some of the experimental vectors do not encode a histological marker, the vectors were co-injected with an equal titer of AAV-CMV-GFP to enable tracing of the infection with the use of the GFP. Control vectors, AAV-CMV-GFP plus AAV-CMV-tdTomato, at the same final titer as the experimental virus injections, were also injected in these cases. A combination of GFP and tdTomato viruses were injected and it was shown that 100% of cones were co-infected, and 85% of all cells in the ONL were co-infected, which is primarily the co-infection rate for rods (FIG. 7). Injections into the sub-retinal space at P0 were made with 0.3 microliters of virus suspension using a pulled glass pipette and Eppendorf picospritzer. Animals were weaned and carried on standard chow and 12 hours light/12 hours dark until the assays described below were performed. The time points for analysis of rd1 mice were 8 weeks (W) and 12W. These time points were chosen based upon the previous descriptions of the kinetics of cone death in rd1 mice, and are the points where approximately no cones remain in the central 50% of the retina (8W) and no cones within approximately 90% of the retina at 12W.

Tests of Expression and Function

To initially test the vectors for protein expression and function, they were assayed on wild-type (WT) retinas. P0 WT mice were co-infected with an equal ratio of AAV-CMV-GFP and an antioxidation vector, and sacrificed at P21. AAV8 is able to express within approximately one week, and most of the infected cells will be rods. The CMV promoter is not as strong in rods as it is in cones, but it is strong enough to see GFP expression immunohistochemically (see, e.g., FIG. 1E), as well as on Western blots. Extracts were prepared for protein analysis, and a Western blot was performed. Commercially available antisera was used (see, e.g., FIG. 2). Controls retinas were infected with only the AAV-CMV-GFP+/− AAV-CMV-tdtomato viruses. To assess how well the vector is expressing, the level of the AAV transduced gene relative to GFP, and relative to the endogenous level of the anti-oxidation gene, was assessed. Since rods are 70% of the cells in the retina, this level was easily visible on the blot.

Figure 3:
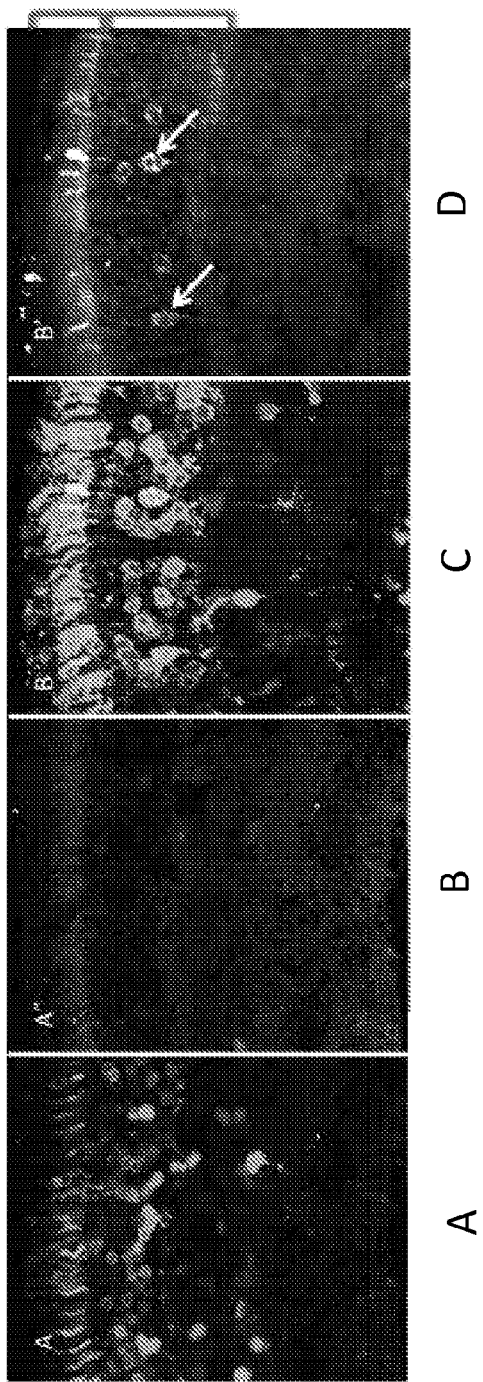
FIGS. 3A-3D depict that knock-down of SOD2 generates oxidation products. An shRNA directed to SOD2, or an irrelevant shRNA, was delivered by electroporation at P0 into WT retinas. A co-electroporated plasmid for identification of electroporated cells was included (CAG-GFP). (A) Cryosection from retina at P30 electroporated with control shRNA, stained with anti-GFP (light gray), and for acrolein, an indicator of oxidized lipids (medium gray). (A') acrolein is shown, and no cells were positive. (B) SOD2 shRNA, stained with anti-GFP and acrolein. (B') All acrolein positive cells were GFP+. Two examples are indicated by arrows. Upper bracket denotes OS and IS, lower bracket the outer nuclear layer (cell bodies of rods and cones).

Infected mice were assessed for the function of the anti-oxidation genes by assessment for oxidization using immunohistochemical detection of acrolein on tissue sections. Sections were processed for acrolein staining, as shown in FIG. 3.

Electroretinography (ERG)

Photopic ERG was conducted as per Komeima et al. (PNAS, 103(30):11300-05, 2006). Generally, rd10 mice with higher b-wave are correlated with greater cone survival.

Mice were dark-adapted overnight and anesthetized, with both pupils dilated. Rod-dominated responses were elicited in the dark with 10-msec flashes of white light ($1.37 \times 10^5$ $cd/m^2$) presented at intervals of 1 minute in a Ganzfeld dome. Light-adapted, cone responses were elicited in the presence of a 41-$cd/m^2$ rod-desensitizing white background with the same flashes ($1.37 \times 10^5$ $cd/m^2$) presented at 1 Hz. ERGs were monitored simultaneously from both eyes, with signal averaging for cone responses.

Behavioral Assays

Behavioral assays include locomotion tests in light and dark environments (see, Collins et al., J of Neurosci Methods, 60(1-2): 95-98, 1995; Legali et al., Nat Neurosci, 11(6):667-75, 2008), forced-choice swim test (see, Prusky et al., Vision Res, 40(16):2201-09, 2000; Wong and Brown, Genes, Brain & Behav 5(5):389-403, 2006), an optomotor test (see, Abdeljalil et al., Vision Res, 45(11):1439-46, 2005; Legali et al., Nat Neurosci, 11(6):667-75, 2008; Prusky et al., Invest Ophthal and Visual Sci, 45(12):4611-16, 2004), and a visual cliff test (see, Nagar et al., Neurosci, 160(2): 517-29, 2009.

The Optomotor device looks like a rotating drum, with a platform in the center. Awake mice were placed on the platform and allowed to habituate to the chamber. This was assessed by whether they jump off of the platform. It typically takes about 5 minutes to habituate the animal to the device. The investigator watched the animals and once they remain on the platform for 1-2 minutes, testing began. To simulate motion, stripes were projected, flashing on and off, onto the inside surface of the drum. The thickness of the stripe, frequency of flashes, contrast, and color were altered over time to determine the visual performance. A video camera was trained onto the mouse to evaluate its response to the simulated movement. Blind mice did not respond; sighted mice increased their body movements, and also turned their heads as if tracking movement. Each mouse was tested a total of 4-6 times over the course of an experiment, which lasted 3 weeks to 6 months. The optomotor test has the advantage that one can measure acuity and sensitivity, which are not easily measured in the other tests. At the termination of the experiment, the animals were tested for ERG prior to sacrifice.

Light-Evoked Ganglion Cell Activity Recording

Animals were dark-adapted over night before being anesthetized. Under infrared illumination to minimize visible light exposure, retinas were dissected and mounted ganglion cell side up on a piece of filter paper in 37 degree oxygenated Ringer medium. The retinas were stimulated with 1 second of visible light (365 nm+505 nm) at an intensity of $10^{10}$ photons $cm^{-2}s^{-1}$. Light-evoked spikes of a single ganglion cell were recorded by an electrode, and responses were averaged by 20 trials.

Histological Analyses

Eyes were enucleated, placed in 4% formaldehyde in PBS, and their anterior segments and lens were removed. Fixation continued in this fixative for 30 minutes. The fixed tissues were soaked in 30% sucrose/PBS for 3 hours or overnight, shock frozen, and sectioned along the superior-inferior meridian at 20 μm thickness. Rhodamine-labeled peanut agglutinin (PNA), red/green opsin, and blue opsin antibodies were used for staining. Stained sections were photographed on a confocal laser scanning microscope. For quantitative comparison, the excitation energy levels and duration of exposure were kept the same for paired samples, and images were taken to preserve the dynamic range of the original signal intensities. Image data were analyzed quantitatively using the ImageJ and Imaris software.

The retinas were assessed histologically using two types of assays to determine the number of cones. A flat mount of the entire retina was generated and scored for the number of bright GFP cells in a consistent area of each retina. Flat mount retinas were oriented based upon a mark made by a cauterizing iron at 12 o'clock, and 4 quadrants were marked off. One square in each retinal quadrant was chosen for quantification, at a distance of 1.5 mm from the optic nerve head, on a line between the optic nerve head and the periphery, as described by Komeima et al. (*PNAS* 103(30): 11300-05, 2006). 60× microscope fields were photographed in each quadrant located at these distances, as exemplified in FIG. 1F. The number of bright GFP+ cells was quantified using Imaris software. Retinal sections were also prepared and stained with anti-cone arrestin and/or PNA binding, along with anti-GFP (FIG. 1B). Sections were made along the dorsoventral axis, in 50% of the retinas, and along the anterioposterior axis, in 50% of the retinas. Two sections near the optic nerve head were quantified for the number of cells positive for the cone marker throughout the entire section. Confocal imaging and Imaris software was used for this analysis. However, in degenerating retinas, it has been found that very dysmorphic cones often are difficult to quantify for cone arrestin and PNA. The bright GFP from the CMV promoter of the virus has provided a more robust way to score, which is why we also stained with anti-GFP.

Example 1

Effects of Antioxidant Enzymes Superoxide Dismutase (SOD2) and Catalase on Cone Cell Death in a Mouse Model of Retinitis Pigmentosa It is generally recognized that cones show signs of oxidation in RP. For example, cones survive longer in mice that have been supplied with anti-oxidants in the diet, or have been transgenically modified to overexpress an antioxidant gene. In addition, it has been shown that catalase, delivered via an Adenovirus vector to RPE cells, protected adjacent photoreceptors from light damage (see, Rex et al., Human Gene Therapy 15(10):960-67, 2004). AAV mediated delivery of anti-oxidant enzymes directly to cones might then protect cones, and in addition, even if all cones are not infected, there may be a benefit to nearby uninfected cones.

Experiments were carried out in rd1 and rd10 null mice at least three times for each strain. These two strains, with different upstream mutations and different kinetics of degeneration, were tested in order to give a greater chance of success, should there be any strain-specific, negative responses. Any positive, reproducible combinations will be tested in AAV vectors with cone-specific promoters.

AAV Vectors Encoding Antioxidant Defense Genes

Figure 8:
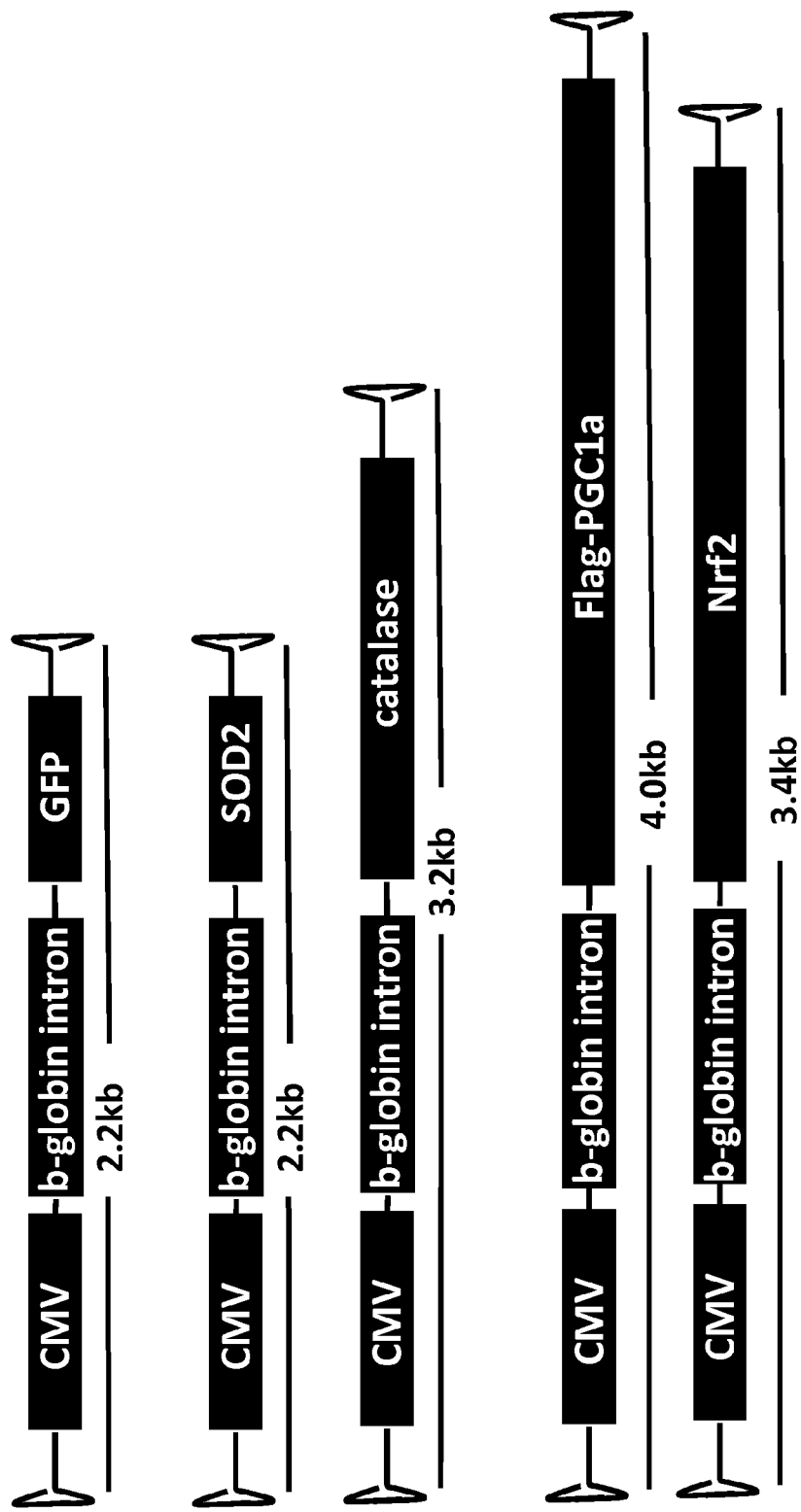
FIG. 8 provides schematics of AAV2/8 vector genomes used for infections. They include a CMV promoter and a beta-globin intron constructed with anti-oxidation genes. To allow for tracking of infected cells, AAV-CMV-GFP was mixed with AAV vectors expressing an antioxidant gene.
Figure 9:
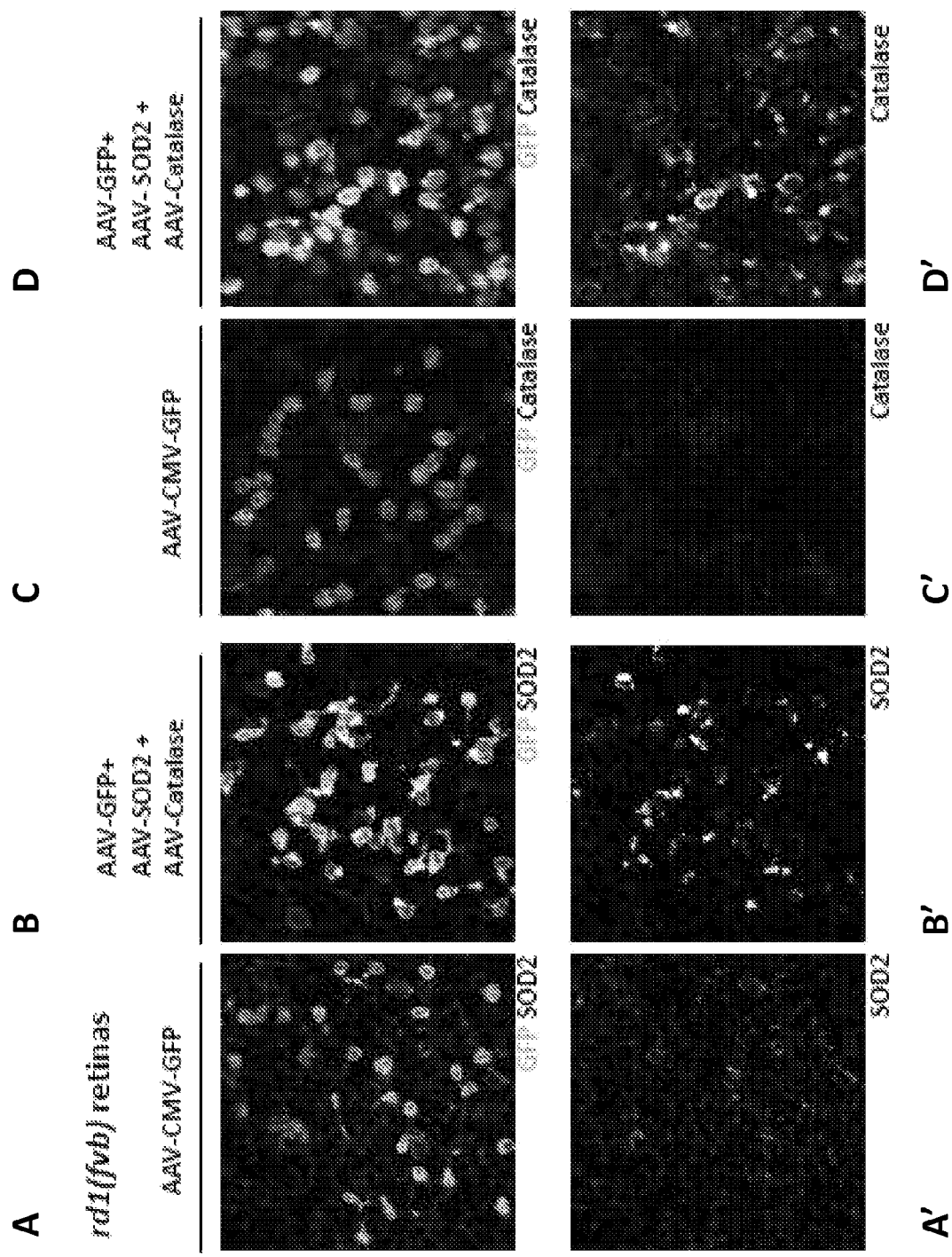
FIGS. 9A-9D depict expression of antioxidant enzymes SOD2 and Catalase by AAV vectors in rd1 retinas. Antisera of antioxidant enzymes (medium gray, A'-D') was applied to cryosections of rd1 P60 retinas and GFP expression (light gray, A-D) was used to track remaining cones. Control rd1 retinas with only AAV-CMV-GFP infection showed little SOD2 (A, A') and Catalase (C, C') expression, while high level of SOD2 (B, B') and Catalase (D, D') expression was evident in the retinas infected with the mixture of three viruses.

Exemplary AAV vectors encoding the antioxidant defense genes, SOD2 and catalase, are depicted in FIG. 8. SOD2, GPX4, and catalase have been implicated in photoreceptor viability (see, e.g., Usui et al., Mol Therap 17(5):778-86, 2009; Ueta et al., JBC 287(10):7675-82, 2012). A catalase allele with the modifications per Usai et al. (Mol Therap 17(5):778-86, 2009), replacing the peroxisome targeting sequence with the mitochondrial targeting sequence from ornithine transcarbamylase has been made. This allele was found to be effective, while the normal peroxisome targeted version was not.

Figure 1:
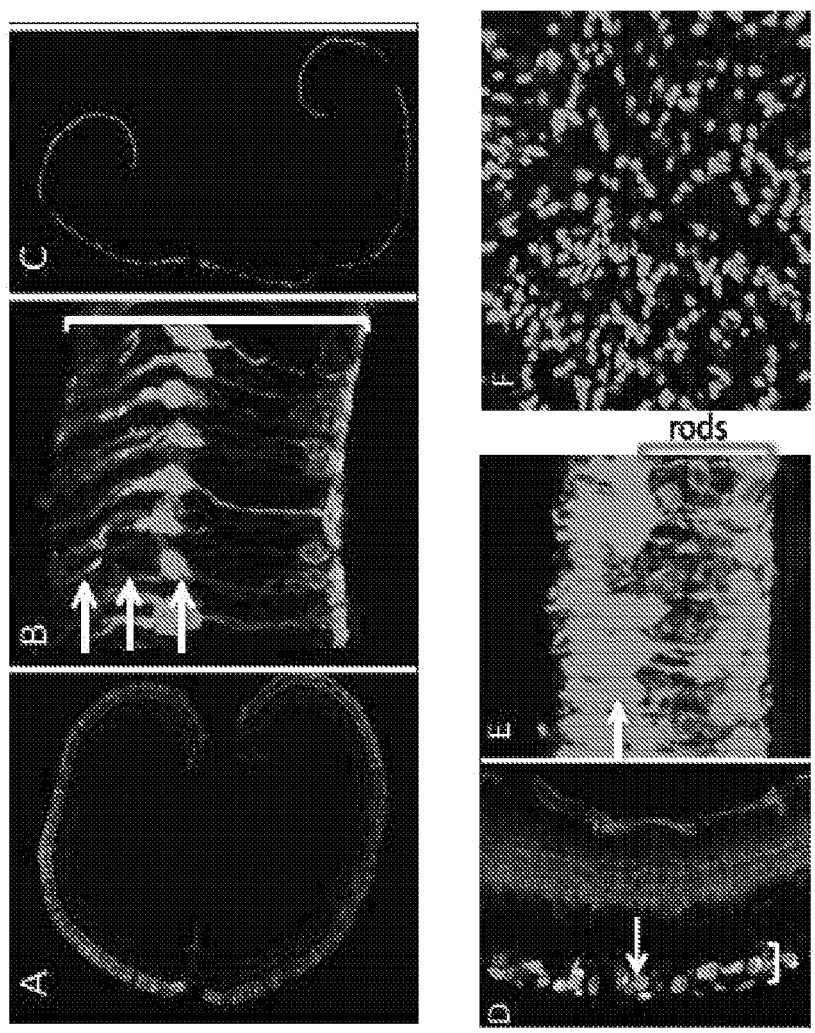
FIGS. 1A-1F depict the infection of WT and rd1 retinas with AAV-CMV-GFP. (A) A WT (wild-type) retina was infected at P0 with AAVCMV-GFP, and harvested at P30. A low magnification image of a cryosection shows extensive spread of the infection throughout the retina. (B) A higher magnification view of the outer nuclear layer in A, showing that cones are well infected and express GFP at a high level (anti-GFP in light gray, PNA—a cone marker—in medium gray). Bracket indicates entirety of cones, with top arrow pointing to cone outer segment (OS) (medium gray PNA stain), middle arrow to cone inner segment (IS) and bottom arrow to cone cell body. (C) Same as A but an rd1 retina was infected. (D) Higher magnification view of C, with remaining cones at P30 well stained with anti-GFP (light gray) and PNA (medium gray). Arrow points to a single cone, and bracket indicates layer of cone cell bodies. (E) Rods from the retina shown in A, visualized by a longer exposure to show that they are infected but express at a lower level (compare to B, with arrow pointing to a cone). (F) Flat mount image of an rd1 retina infected with AAV-CMV-GFP at P0. A 60+ (250 micron square area) image taken 1 mm from the optic nerve head, with the focal plane in the remaining outer nuclear layer is shown, to represent the type of quantification that was carried out in retinas infected with experimental viruses.
Figure 2:
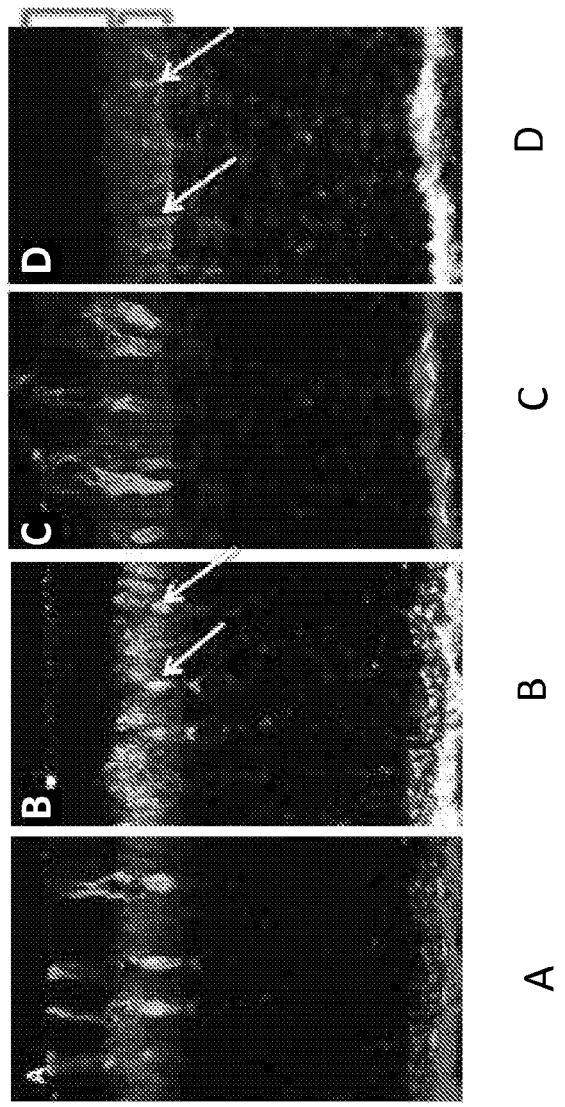
FIGS. 2A-2D depict endogenous expression of anti-oxidation enzymes in the WT retina. Antisera was applied to cryosections of WT P30 retinas (medium gray) and anti-PNA was used to identify cone OS (light gray). (A) Anti-SOD2 and anti-PNA, (B) anti-SOD2 to highlight staining in cone OS, (C) Anti-Gpx1 and anti-PNA, (D) anti-Gpx1 only. Arrows indicate cones. Upper bracket in D denotes area of OS and lower bracket area of cone cell bodies and IS.

The vectors were packaged in AAV capsid type 8, with a tyrosine mutation in the C-terminal tyrosine, which augments infectivity of the virus preparation. Site-directed mutagenesis was used to create this capsid allele. Production and purification of such vectors were done using an Iodixinol gradient centrifugation, followed by ion exchange column purification. The final titers range from $10^{12}$-$10^{14}$ virus particle (vp)/ml and have excellent infectivity (FIGS. 1 and 7).

Results

AAV Vectors

AAV vectors have been used successfully in patients with, e.g., Leber's congenital amaurosis. Thus, these vectors were chosen for the delivery of genes to RP retinas. The promoters that can be used with AAV must be relatively small, owing to a rather limited capacity of the virus of about 4.7 Kb of DNA. CMV, although a fairly broadly expressed promoter, is more active in cones than in rods (FIG. 1B, E). In addition, CMV can drive high level expression in the RPE. If there are excess free radicals in the RPE as well as in the retina, this might have the benefit seen in a study in which Adenovirus was used to transduce the RPE with catalase (see, Rex et al., Human Gene Therapy 15(10):960-67, 2004). Thus, CMV was chosen for the initial experiments. By injecting at P0 rather than older stages, it was found that virtually every cone is infected throughout the retina, when the virus is accurately delivered to the subretinal space, which occurs in about ⅔ of the animals (FIG.

1A-D). This wide dissemination of virus is likely due to 2 causes. One is that the P0 retina subretinal space is relatively open due to the lack of OS and RPE connections at this early stage before OS are present. The viral inoculum is thus free to diffuse from the inoculation site. Furthermore, the cones are situated near the scleral side of the subretinal space, and there is not a layer of OS and inner segments (IS) that might interfere with virus diffusion and entry into the cells. They are, thus, readily accessed by the viral particles. In fact, this injection protocol was found to be so robust, and the CMV-GFP so bright, that the number of bright GFP cells can be used as a proxy for cone survival (FIG. 1F). This allowed a relatively rapid assessment of cone survival following delivery of test genes. Such results were followed up by staining for the cone markers, cone arrestin or PNA, in a secondary screen (FIG. 1B).

Anti-Oxidation Enzymes

The expression of anti-oxidant enzymes in wild type (WT) and RP retinas (rd, generally) during the course of degeneration (FIG. 2) was examined. The conversion of free radicals of oxygen to $H_2O_2$ is carried out by the SOD enzymes, SOD1-3. Following this reaction, $H_2O_2$ is converted to water and oxygen by catalase or glutathione peroxidase. As the electron transport chain in mitochondria is a major source of free radicals in all cells, and photoreceptors are known to have one of the highest densities of mitochondria of all cell types in their IS, it is no surprise that high levels of GPX1 and SOD2 were found in the IS of photoreceptors (FIG. 2A-D).

Figure 4:
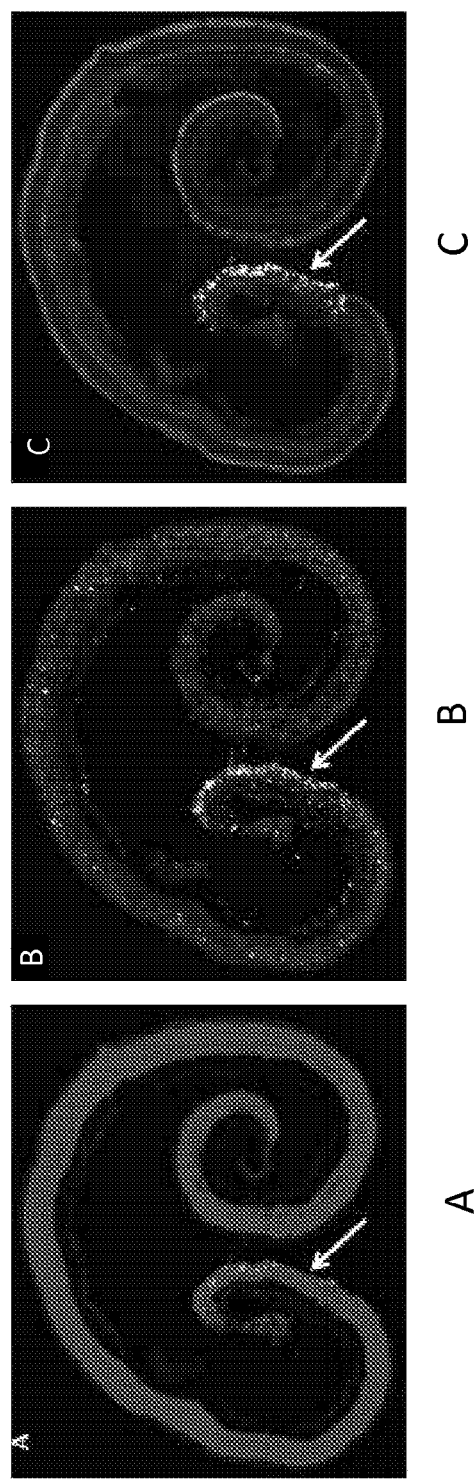
FIGS. 4A-4C depict that knock-down of Gpx1 leads to rapid cell death. An shRNA directed to Gpx1 was delivered by electroporation at P0 into WT mice. A co-electroporated plasmid for identification of electroporated cells was included (CAG-GFP). (A) A low magnification cryosection from retina at P30 stained with DAPI (medium gray area), with electroporated region indicated by the arrow. (B) TUNEL staining revealed positive cells in the area of electroporation. (C) Anti-GFP shows area that was electroporated is the area with TUNEL+ cells. Control shRNA showed very few TUNEL+ cells (not shown).

After making these observations, it was determined whether rod photoreceptors relied on SOD2 or GPX1 for their survival. To this end, small hairpin (sh)RNA plasmids were delivered to WT retinas using electroporation at P0 (see, Matsuda and Cepko, PNAS 104(3):1027-32, 2007). This method targets primarily mitotic progenitor cells, which pass the plasmids on to the daughter cells, 80% of which are rods. (Cones are post-mitotic at this time and are not electroporated effectively.) The hairpin plasmids were co-electroporated with a plasmid expressing GFP, under the ubiquitous CAG promoter. There was a higher level of oxidized lipids, as revealed by acrolein staining, in retinas with SOD2 knock-down (FIG. 3). The rods electroporated by the GPX1 shRNA died, as seen by TUNEL staining (FIG. 4). These data support the hypothesis that photoreceptor cells require robust anti-oxidation capacity. It is interesting that death occurred very rapidly upon loss of a single anti-oxidation enzyme, suggesting that these enzymes are not redundant. This may be due to their different activities, as GPX4 is more active in lipid oxidation while GPX1 is not known to have any specific molecules that it targets. Further, enzyme localization may be important as anti-oxidation enzymes can target different compartments, i.e. mitochondria, cytoplasm, or peroxisomes.

Thus, two sets of vectors were made. In one set, two anti-oxidation defense genes were expressed from the same AAV vector. To track such infections, co-infection with an AAV-CMV-GFP was used. As shown in FIG. 1, AAV-CMV-GFP is very bright in cones and allows quantification, and as shown in FIG. 7, co-infection rates are high. In a second set of vectors, the two anti-oxidation defense genes were expressed from two different AAV vectors, with GFP included in at least one of the vectors. The advantage of having the genes in two different vectors is that it enables testing of various combinations of anti-oxidation genes, and testing of only single gene.

Figure 10:
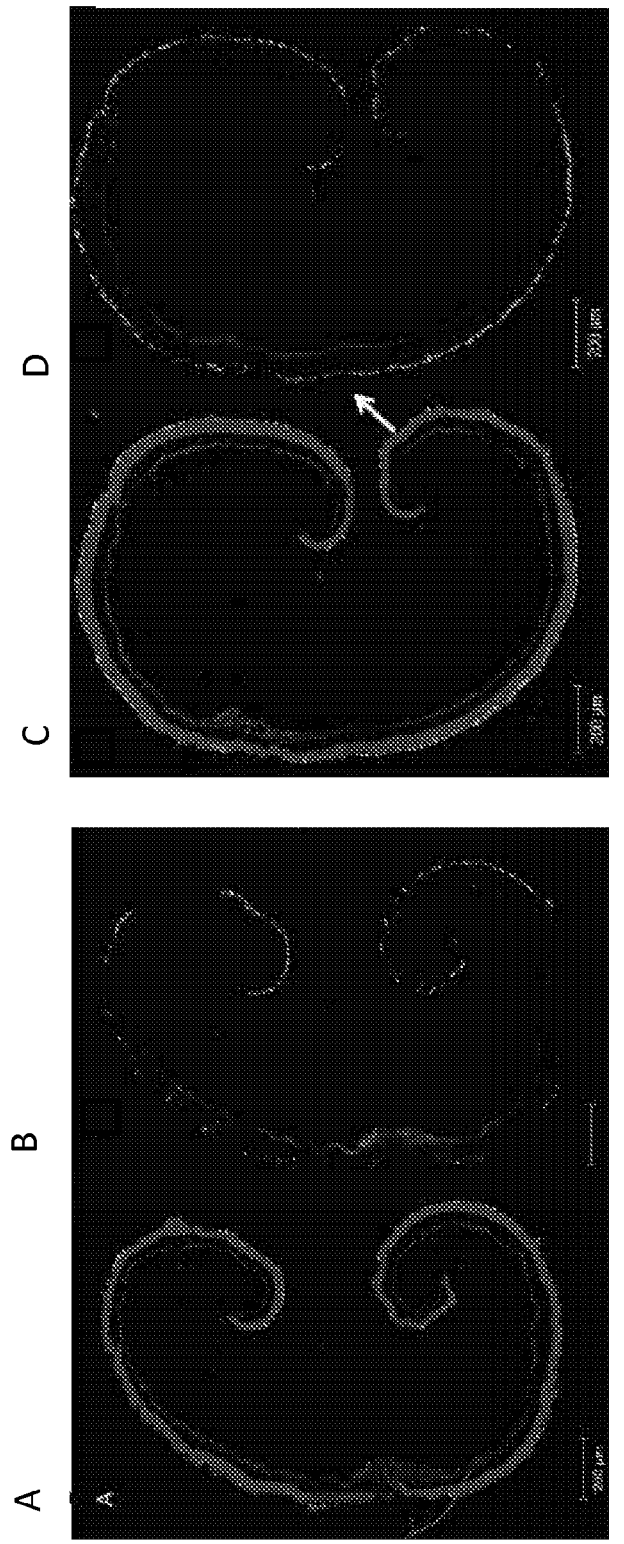
FIGS. 10A-10D depict that delivery of anti-oxidation enzyme genes by AAV promotes cone survival. A P0 rd1 retina was co-infected sub-retinally with AAV-CMV-GFP, AAV-CMV-SOD2- and AAV-CMV-catalase (vectors shown in FIG. 8). Control rd1 retinas were infected with AAV-CMV-GFP. At P50, cryosections were prepared and sections through the central retinas were imaged for GFP (light gray, B, D). Retinal section infected with control virus (A, B). Note absence of GFP+ cells in the central retina (B). Retinal section infected with anti-oxidation viruses (C, D). Note that there are GFP+ cells in the central retina (arrow, D), in the scleral location, indicative of cone cell bodies (e.g., see FIG. 1D).
Figure 11:
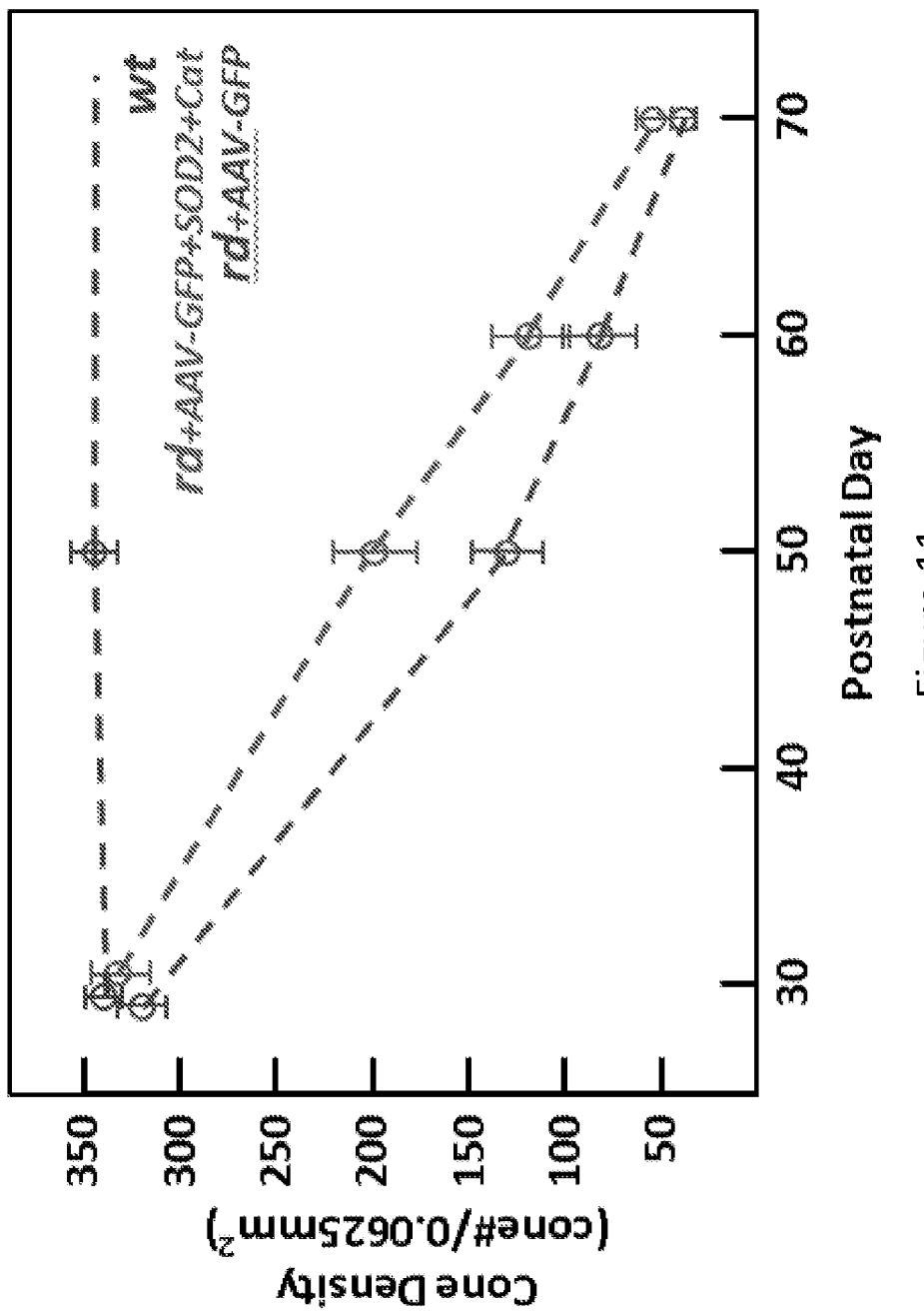
FIG. 11 demonstrates that overexpression SOD2 and Catalase prolongs cone survival. The average cone densities in WT and rd1 retinas infected with AAV vectors expressing SOD2 and Catalase were shown. Cone density was quantified in four 250 μm×250 μm squares at 1.5 mm dorsal, ventral, nasal and temporal to the center of the optic nerve head in each retina, and around 20 retinas were analyzed per group per time point. Adult WT retinas have a constant cone density (~350 cones per 0.0625 mm$^2$). The mean (±SEM) cone density was greater at P50, P60 and P70 and was significantly greater (p<0.05) at P50 in the rd1 retinas treated with AAV-CMV-GFP, AAV-CMV-SOD2 and AAV-CMV- Catalase (medium gray line) compared to the control retinas with only AAV-CMV-GFP (dark gray line).
Figure 12:
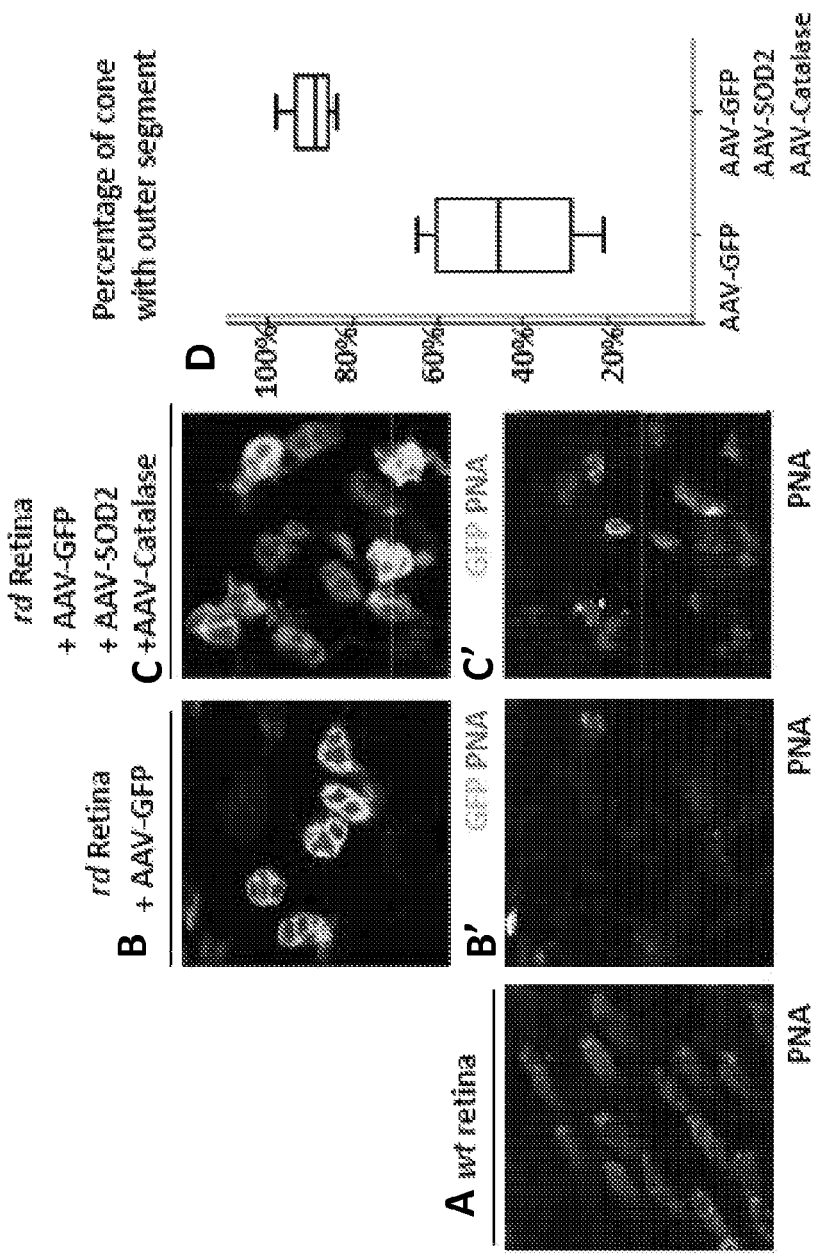
FIGS. 12A-12D demonstrate that overexpression of SOD2 and Catalase preserves outer segments (OS) and inner segments (IS) of cones. High magnitude images of flat-mounted P60 WT and rd1 retinas infected with AAV vectors expressing SOD2 and Catalase. Retinas were stained with anti PNA (medium gray, A, B', C') to show cone OS and IS. While long OS and IS (A) were present in WT retina, the remaining cones (marked by GFP, light gray, B) in rd1 P60 retina lack OS and IS (B'). Overexpression of SOD2 and Catalase rescued cone OS and IS (C and C') in rd1 P60 retinas. The phenotype was quantified by counting the percentage of cones with PNA staining. Numbers were shown as mean±s.d. n=3 retinas per group.

Data from co-infection of P0 rd1 retinas with AAV-CMV-SOD2 and AAV-CMV-catalase show greater cone survival at P50 in rd1 mice co-infected with these vectors (FIGS. 10 and 11). The number of bright GFP cells in the scleral portion of the retina in sections taken through the central portion of the retina was quantified. The number of bright GFP+ cells in the control was 259+/−113 cones/section, and the number in the SOD2+catalase infected retinas was 342+/−29.3 cones/section. Additionally, SOD2 and catalase co-overexpression in rd1 retinas show improved cone survival. At all the time points examined (P30, P50, P60, and P70), the cone density in retinas overexpressing SOD2+catalase is higher than that in retinas with GFP overexpression. At postnatal day 50, the cone density in retina overexpressing SOD2+catalase is approximately 1.5-fold higher (196+/−22.3 cones/0.0625 $mm^2$ vs 133+/−60 cones/0.0625 $mm^2$, p value21 0.02) (FIG. 11). Further, cone outer segments, where phototransduction is carried out and which is an important index for cone function, were better preserved in rd retina upon SOD2+catalase co-overexpression (FIG. 12). While cone outer segments are comprised in rd1 retinas at postnatal day 60 (FIG. 12B), they are present in most remaining cones in retinas with SOD2 and catalase overexpression (FIG. 12C). Quantification of this phenotype showed a great increase in the percentage of cones with obvious PNA staining in retinas with SOD2 and catalase overexpression (FIG. 12D).

Figure 13:
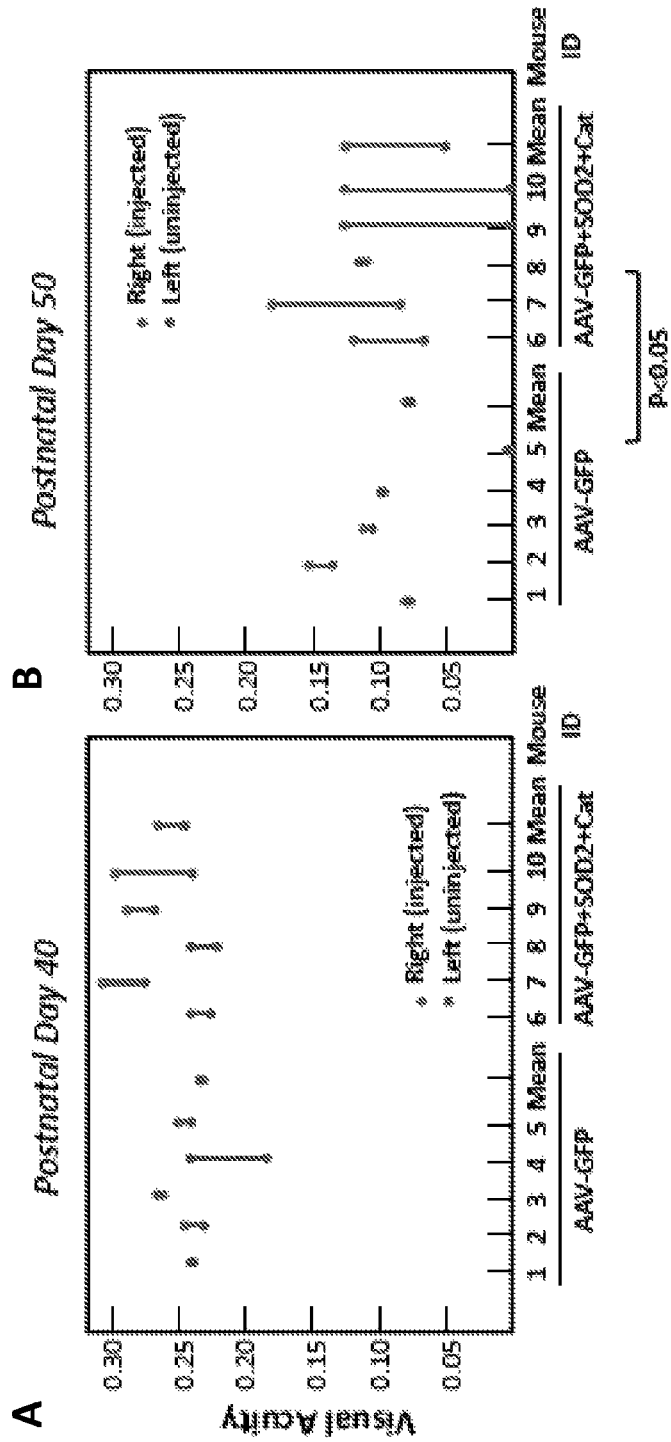
FIGS. 13A-13B demonstrate that overexpression of SOD2 and Catalase preserves photoreceptor function as measured by optomotor assay. Shown are the visual acuity of uninjected left eyes (medium gray) and AAV vectors injected right eyes (light gray) of rd10 mice. Control treated mice with AAV-CMV-GFP (mouse ID 1-5, n=5) and AAV-CMV-GFP+AAV-CMV-SOD2+AAV-CMV-Catalase treated mice (mouse ID 6-10, n=5) were tested at P40 (A) and P50 (B). At P40 and P50, most antioxidant treated mice tested had higher right eye visual acuity than left, while most control treated mice have similar left and right eye response. The differences of left and right eyes between the two groups (control treated vs antioxidant AAV treated mice) were significant at P50 (P<0.05) (B).
Figure 14:
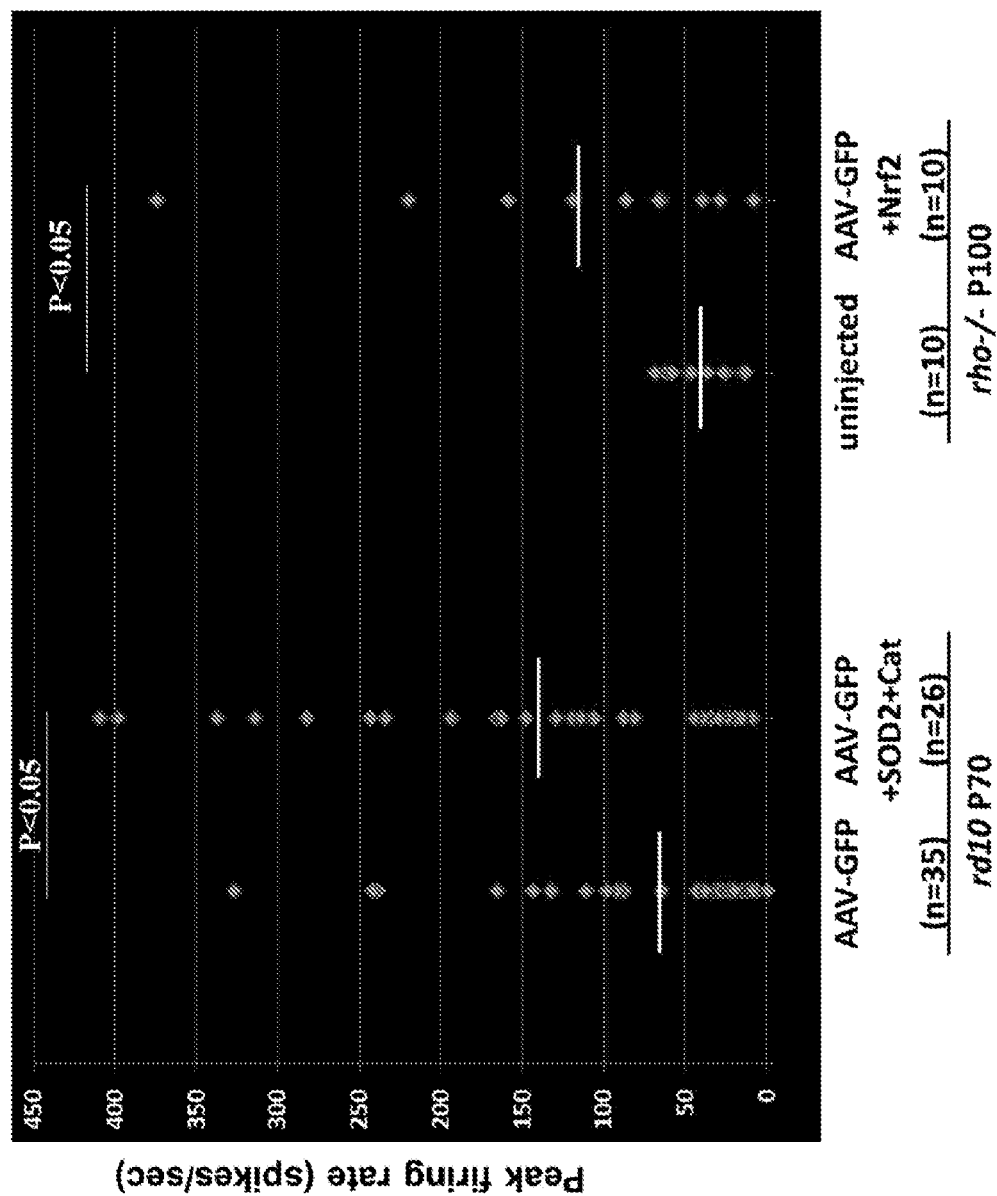
FIG. 14 demonstrates that overexpression of SOD2 and Catalase preserves photoreceptor function as measured by light-evoked ganglion cell activity. The left side of the graph shows the results of retinas from rd10 mice treated with AAV-CMV-GFP and AAV-CMV-GFP+AAV-CMV-SOD2+AAV-CMV-Catalase that were harvested at P70 for ganglion cell activity recording. Data presented are from a total of 35 ganglion cells from 3 control treated retinas and a total of 26 cells from 3 antioxidant AAV vector treated retinas.

Moreover, mice overexpressing both SOD2 and catalase exhibited better overall photoreceptor function as assessed by optomotor response (FIG. 13) and light-evoked ganglion cell activity (FIG. 14). Shown by optomotor assay, the injected eyes with AAV vectors encoding SOD2 and catalase have higher visual acuity compared to both the uninjected eyes and the control injected eyes at postnatal days 40 and 50 (FIG. 13). At postnatal day 50, the difference of left and right eye acuity (right eye acuity-left eye acuity) is statistically significant between the control group and antioxidant AAV treated group (0.0044 cycle/degree vs 0.0834 cycle/degree, P<0.02) (FIG. 13B). In addition, retinas overexpressing SOD2 and catalase had increased light-evoked activity of ganglion cells (FIG. 14, left-hand side). Light response of surviving cones was assessed by ganglion cell activity, which is the output signal from retina to brain. The parameters (wavelength and intensity) of light stimulus were selected to activate cone photoreceptors but not intrinsically photosensitive retinal ganglion cells (ipRGCs). The average ganglion cell activity, measured by peak firing rate (spikes/second), was higher in retinas with SOD2 and catalase overexpression than in control retinas (106 spikes/sec vs 38.7 spikes/sec, p<0.005) (FIG. 14). The mice that received antioxidant gene therapy will be further tested through other functional assays, including light-dark box assay, visual cliff assay, and electroretinography.

The ability of anti-oxidant treatment to rescue cones in other retinal degeneration models was tested by treating six month old rho−/− mouse retinas with AAV-GFP+SOD2+Catalase. The results shown in FIG. 25 demonstrate that anti-oxidant treatment can be used to treat multiple mutations that lead to blindness.

Example 2

Figure 5:
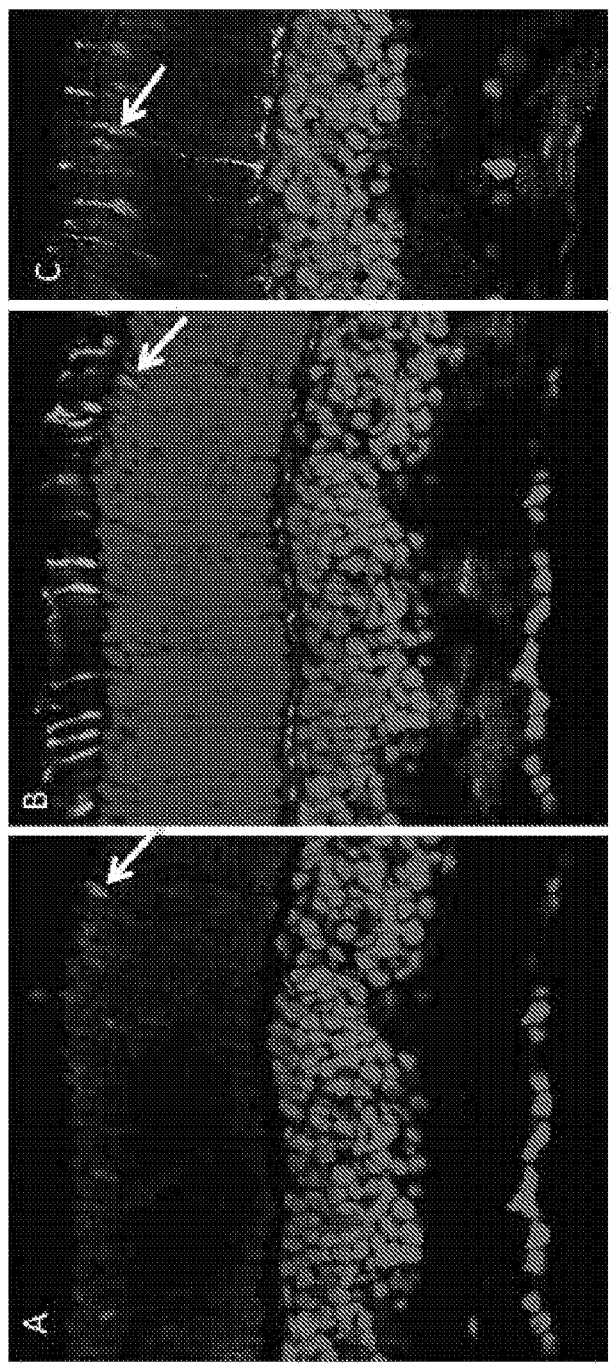
FIGS. 5A-5C depict endogenous expression of PGC1α in the retina. A WT adult retina was stained with anti-PGC1α. Most nuclei were positive, with higher expression in cones than in rods. (A) Anti-PGC1α in medium gray showing nuclear localization in most retinal cells (arrow in panel A, and circular medium gray staining). (B) Same section as (A) but showing expression in cones using anti-PNA (light gray, e.g., light vertical lines at top of panel B) and nuclei (dark gray, DAPI, e.g., the large area in which the arrow lies). Arrows show a cone nucleus. (C) Staining of a different section with anti-cone arrestin (light gray) and anti-PGC1α shows cone staining as well. Arrow shows an example of a double stained cone.

Effects of Transcription Factors PGC1α and Nrf2 on Cone Cell Death in a Mouse Model of Retinitis Pigmentosa Alternatively, or in combination with expression of at least one antioxidant enzyme, a general upregulation of the anti-oxidation program may provide greater cone survival (e.g., by up-regulation of the expression and/or activity of PGC1α and Nrf2). The expression of PGC1α was examined using immunohistochemistry in WT retinas (FIG. 5). The protein was found at a fairly high level in all retinal neurons, with a higher level seen in cones than in rods.

An alternative master regulator is Nrf2, a basic leucin zipper transcription factor. Nrf2 is part of the endogenous cellular stress defense mechanism and also has been shown to regulate transcription of anti-oxidation enzymes. Nrf2 is usually kept at low levels in healthy cells by its cytoplasmic binding partner Kelch-like ECH-associated protein 1 (Keap1) protein via ubiquitin-dependent degradation. Upon activation by oxidants, Keap1-mediated Nrf2 turnover is disrupted, and Nrf2 accumulates and translocates to the nucleus, where it modulates the transcription of antioxidant genes with small Maf proteins through the antioxidant response element (ARE). The ARE is a cis-acting enhancer found in the 5' region of many antioxidant genes.

The cDNA for the mouse PGC1α allele (2.4 Kb) was inserted into the AAV2/8 vector system, allowing for expression of the PGC1α protein under the control of a CMV promoter. PGC1α expression from AAV-CMV-PGC1α was assayed using both Western blots of transfected, cultured cell lines, and by immunohistochemistry on infected retinas upon infection of B16J retinas at P0. To determine PGC1α functionality, the expression level of some of its known target genes was assayed using semi-quantitative RT/PCR. Briefly, retinal RNA preparations at P21 are obtained using standard methods (RNAeasy kit, Qiagen) and the levels of SOD2, GPX1 and 4, catalase and uncoupling protein (UCP) are compared between control-infected and PGC1α-infected retinas. Assays for greater oxidation protection (acrolein and ELISA for carbonyl adducts) are also conducted, as described above, following challenge by paraquat.

The full-length allele of the mouse Nrf2 gene was obtained from Addgene. An AAV2/8 vector expressing the Nrf2 protein driven by the CMV promoter was produced. Its expression was confirmed by Western blot on cultured cell lines transfected with AAV-CMV-Nrf2 plasmid, followed by immunohistochemistry on infected retinas. RT/PCR for several target genes was carried out as described above.

Results

Figure 6:
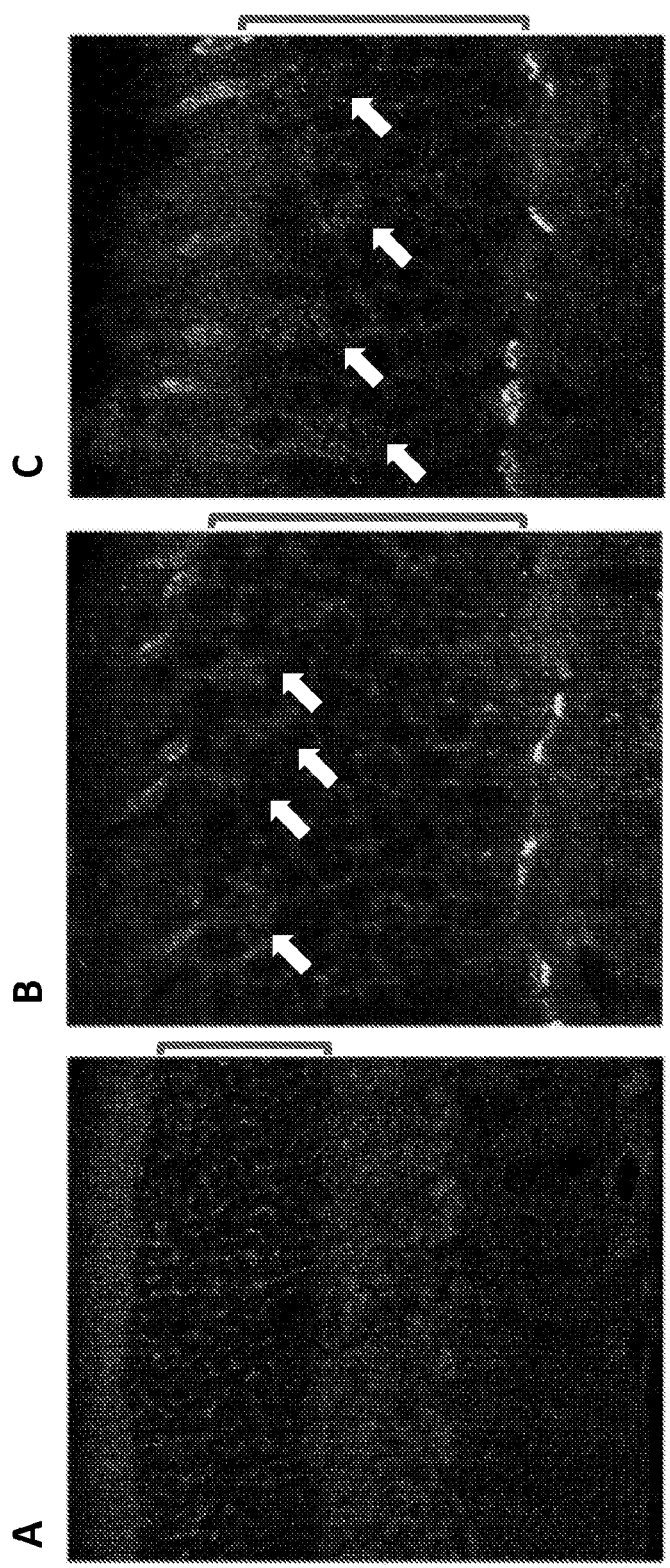
FIG. 6A-6C depict endogenous expression of Nrf2 in the WT, rd10 and rho−/− retinas. Antisera of Nrf2 protein was applied to cryosections of WT P30 retinas (medium gray) and anti PNA was used to identify cone OS (light gray). Low level of Nrf2 (gray) is expressed in IS, outer nuclear layer (ONL) and inner nuclear layer (INL) in WT retina (A). Nrf2 level (medium gray) is elevated in cones (higher than rods) in rd10 P18 retinas (B) and rho−/− P30 retinas (C). Arrows point out the cone somas with higher level of Nrf2 protein. Brackets in B and C denote ONL layer.

PGC1α protein is expressed in most retinal cell types, with a higher level in cone photoreceptors than rods (FIG. 5). As PGC1α positively regulates the mitogenic and anti-oxidant pathways, its expression pattern indicates a higher metabolic demand and a requirement for greater antioxidant capacity of cones. Nrf2, on the other hand, is expressed at a very low level in photoreceptors and other retinal cells in normal retinas (FIG. 6A). However, during the rod photoreceptor cell death phase of the retinal degeneration, the Nrf2 protein level was elevated as assessed by immunohistochemistry (FIGS. 6B-C). As described before, the Nrf2-Keap1 system functions as a cellular sensor for oxidants. Thus, elevated Nrf2 levels suggest higher oxidative stress and a greater need to cope with oxidants in cones during rod degeneration. This increase of Nrf2 protein level in cones during retinal degeneration was observed in two different rd mouse models with distinct genetic mutations, suggesting that increasing oxidative stress in cones is a general problem for retinal degeneration diseases, including retinitis pigmentosa.

Figure 15:
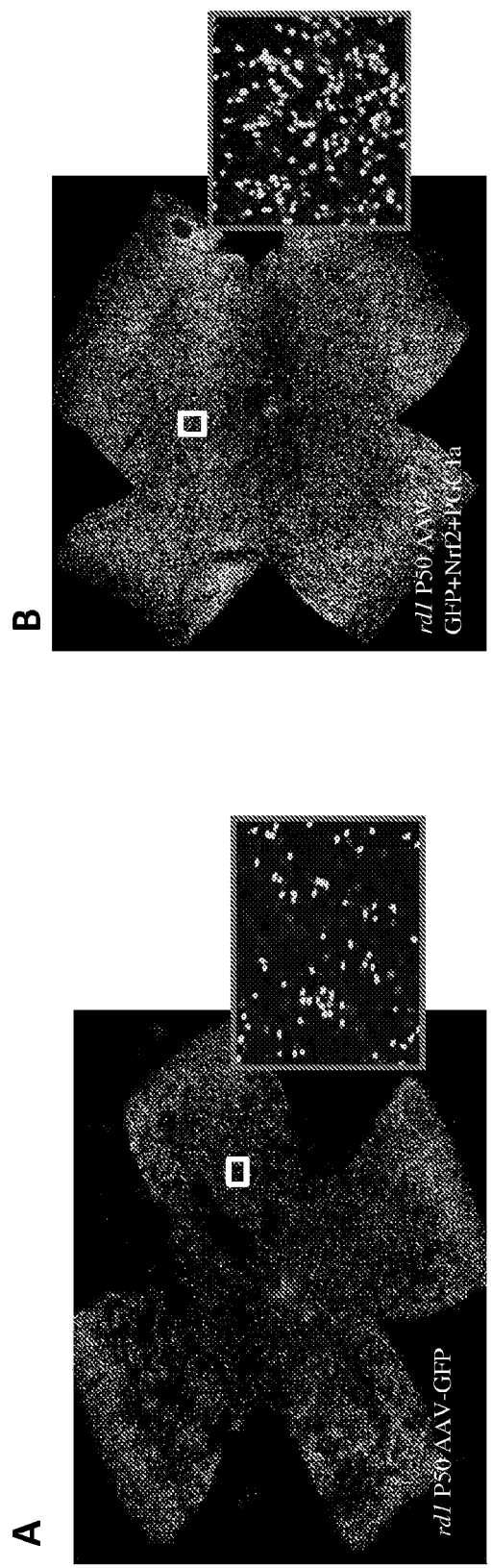

Co-overexpression of PGC1α and Nrf2 by AAV vectors prolongs cone survival in rd1 retinas at P50 (FIG. 15). At P50, most of the cone photoreceptors that have died are in the central area of retinas, as the degeneration progresses from the center to the periphery in rd mouse retinas (FIG. 15A). Overexpression of PGC1α and Nrf2 rescued cone survival in the central retina at P50 (FIG. 15B).

Quantification of the rescue phenotype showed that PGC1α and Nrf2 overexpression rescued cone survival, with a significantly higher cone density in treated retinas than control retinas (273+/−6 cones/0.0625 $mm^2$ vs 133+/−60 cones/0.0625 $mm^2$, $p<0.05$) (FIG. 16).

In addition, PGC1α and Nrf2 co-overexpression promoted cone survival better than co-overexpression of SOD2 and catalase ($p<0.001$) at P50. Furthermore, this rescue remained significantly higher than that of the control retinas ($p<0.05$) at P80 (FIG. 16).

Data from co-infection of P30 rd1 retinas transfected with AAV-CMV-PGC1α and AAV-CMV-Nrf2 show that PGC1α and Nrf2 co-overexpression preserves cone outer segments in rd1 retinas at P30 (FIGS. 17 and 18), P40 and P50. Quantification of the cone outer segments showed that Nrf2 overexpression preserved cone outer segments, with a significantly higher percentage in treated retinas than control retinas ($p<0.05$) (FIG. 20).

Figure 22:
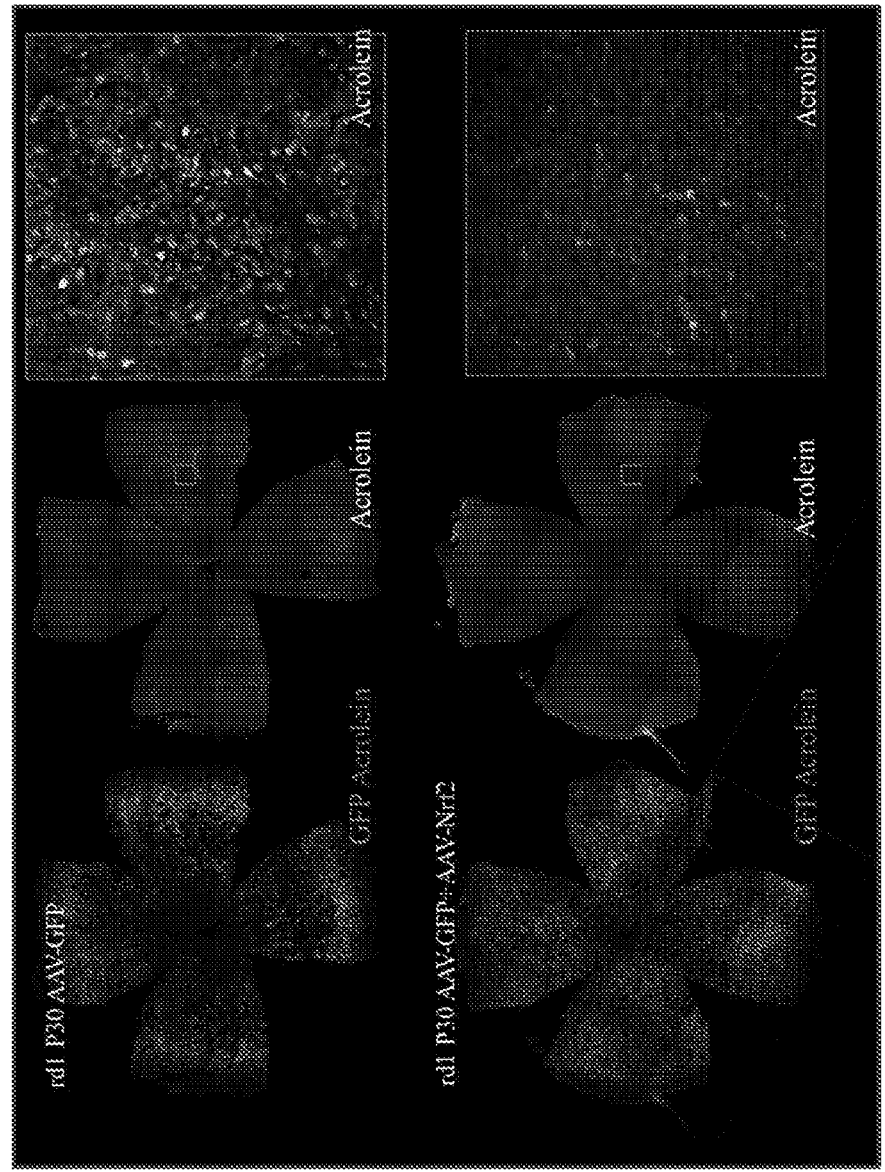

Additionally, overexpression of Nrf2 alone, prolonged cone survival in rd1 retinas at P50 (FIG. 19). At P50, the mean cone density in retinas overexpressing Nrf2 was higher than that in retinas with either PGC1α alone or with Nrf2 and PGC1α. Moreover, treatment of Nrf2 showed that superoxide levels were reduced upon addition of Nrf2 to rd10 mice at P45 (FIG. 21), and overexpression of Nrf2 reduced lipid oxidation in cones in rd1 mice at P30 (FIG. 22).

Figure 23:
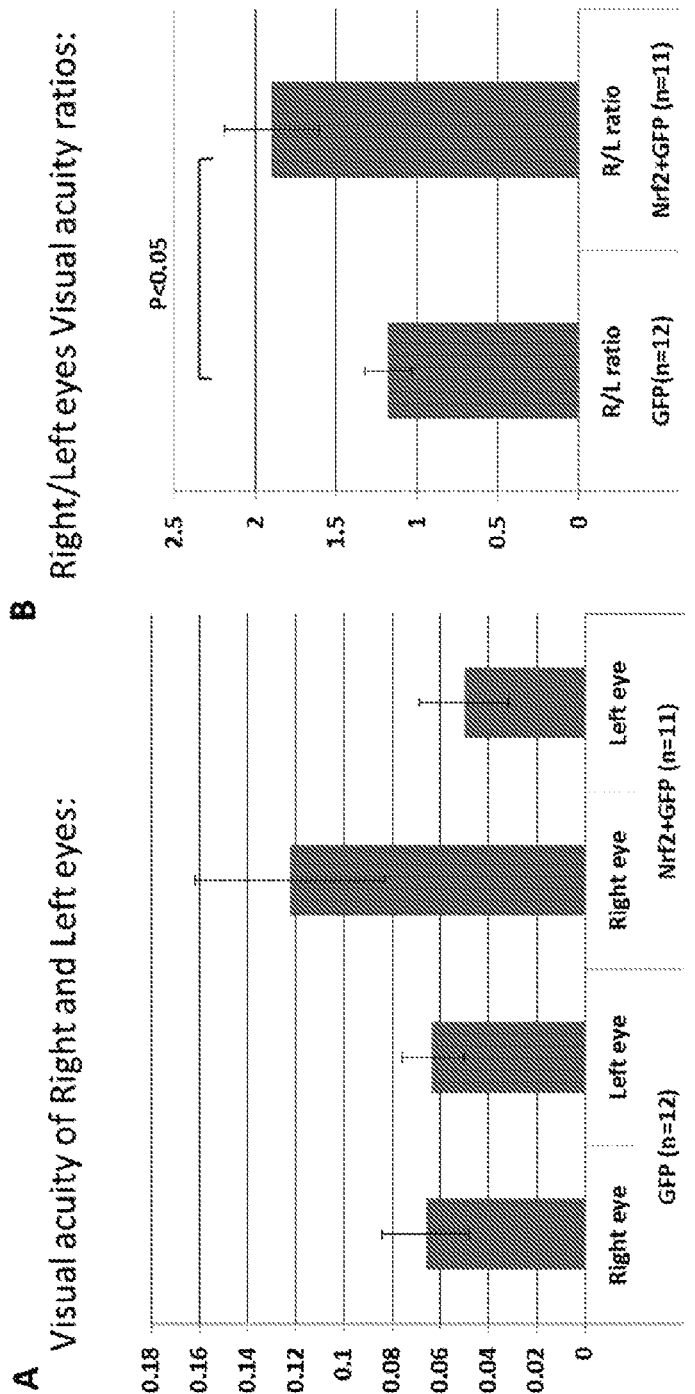
Figure 24:
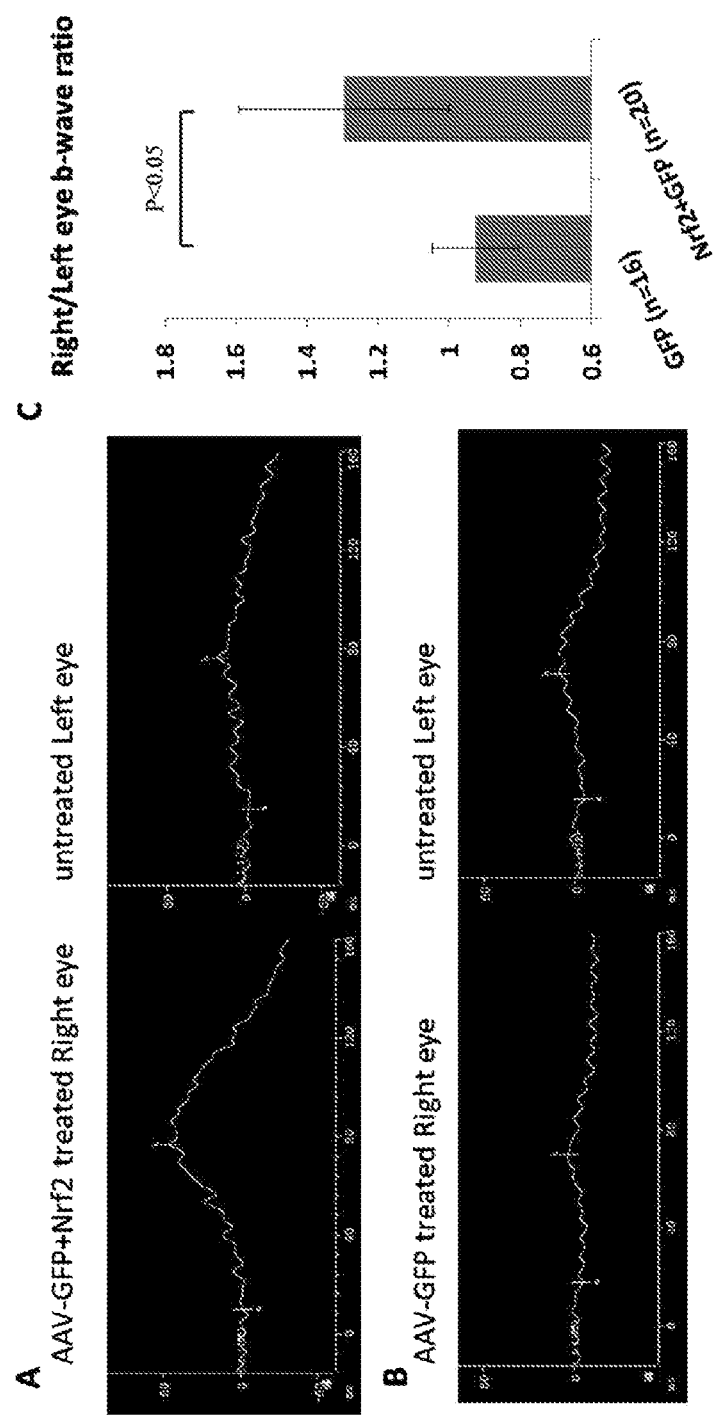

Furthermore, mice overexpressing Nrf2 were shown to exhibit better overall photoreceptor function as assessed by optomotor assay (FIG. 23), electroretinography (FIG. 24) and light-evoked ganglion cell activity (FIG. 14, right-hand side). Shown by optomotor assay, the injected eyes with AAV vector encoding Nrf2 have higher visual acuity compared to both the uninjected eyes and the control injected eyes at P50 (FIG. 23). The ratio of Right eye/Left eye visual acuity of each animal was used to minimize the variation between animals without treatment. The R/L ratio of AAV-CMV-Nrf2 treated retinas was significantly higher than that of the control treated retinas ($p<0.05$). In addition, retinas overexpressing Nrf2 had a substantially better waveform as shown by electroretinography analysis. The ratio of right eye/left eye b-wave amplitude was significantly higher in Nrf2 treated mice than that in the control mice (FIG. 24).

Retinas overexpressing Nrf2 also had increased light-evoked activity of ganglion cells (FIG. 14). Light response of surviving cones was assessed by ganglion cell activity as described above. The average ganglion cell activity was higher in retinas with Nrf2 overexpression than in control retinas (FIG. 14). Results from these functional assays demonstrate that cone function in mouse models of retinitis pigmentosa was preserved upon Nrf2 treatment.

Example 3

Effect of the Transcription Factor Nrf2 and the Antioxidant Enzyme Superoxide Dismutase (SOD2) on Retinal Ganglion Cells The retina is a structure with one white matter tract, the optic nerve, connecting the retinal ganglion cells (RGCs) to their targets within the brain. The isolation of these axons from surrounding gray matter provides a unique opportunity to create a pure axonal injury by crushing the nerve to use as a model for glaucoma (see, e.g., Templeton and Geisert (2012) Mol Vision 18:2147-2152). Optic nerve crush (ONC)

has advantages over other methods, such as optic nerve transections, for it is relatively mild and does not interrupt ocular blood flow. The ONC is particularly useful as a simple synchronous approach for examining ganglion cell injury in a large number of mouse strains. This experimental model produces an insult with the same molecular changes that occur in murine models of glaucoma where there is both an induced and/or intrinsic elevation of intraocular pressure.

Figure 26:
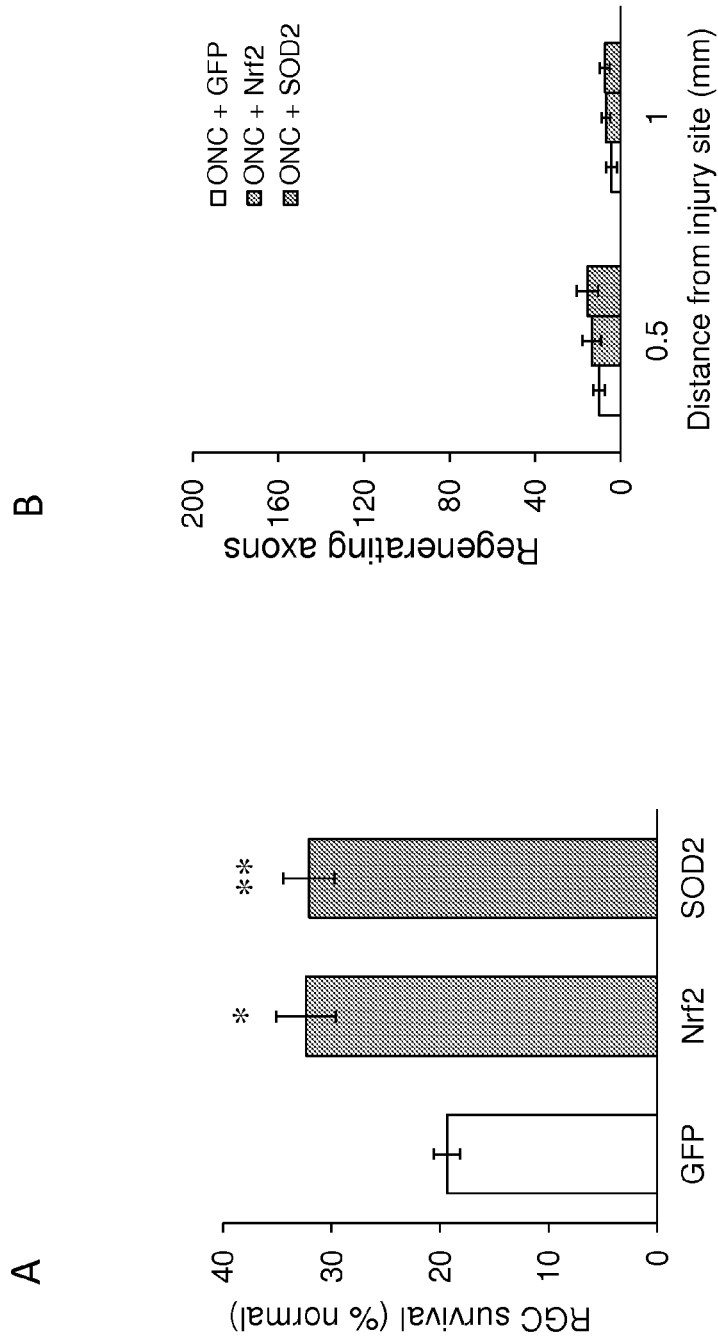

Accordingly, the effect of increased expression of the antioxidant defense proteins, Nrf2 and Sod2, on the survival of RGCs following optic nerve crush, was examined. Wild-type mice whose one eye was infected with AAV2-GFP (n=4), AAV2-Nrf2 (n=8), or AAV2-Sod2 (n=8) two weeks prior, were anesthetized and the optic nerve was crushed. Two weeks after crush, the animals were sacrificed, flat mounts of the retinas were prepared, and the number of RGCs were counted by immunohistochemical staining with an RGC marker, neuronal beta III/tubulin marker TUJ1, and an axonal regeneration marker, GAP43. As demonstrated in FIG. 26, although treatment with Nrf2 or Sod2 did not increase axon regeneration (FIG. 26B), both Nrf2 and Sod2 significantly promoted RGC survival, as compared to treatment with AAV2-GFP (FIG. 26A). Accordingly increased expression of one or more antioxidant defense proteins is useful for treating a retinal disorder, such as glaucoma in a subject.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition formulated for intraocular administration, comprising a recombinant adeno-associated virus (AAV) comprising a promoter operably linked to a nucleic acid molecule encoding nuclear factor erythroid 2-like 2 (Nrf2) in an amount effective for promoting photoreceptor survival and/or function and a pharmaceutically acceptable carrier for intraocular administration,
wherein the promoter is a retinal pigment epithelial-specific promoter, a rod-specific promoter, a cone-specific promoter, or a rod- and cone-specific promoter,
wherein the recombinant AAV is an AAV8 or AAV 2/8 recombinant AAV, and wherein the pharmaceutical composition is formulated for intraocular administration.

2. The composition of claim 1, wherein the promoter is selected from the group consisting of an Nrl promoter, a Crx promoter, a Rax promoter, a cone opsin promoter, an interphotoreceptor retinoid binding protein (IRBP156) promoter, a rhodopsin kinase (RK) promoter, a neural leucine zipper (NRLL) promoter, a cone arrestin promoter, a Cabp5 promoter, a Cralbp promoter, and combinations thereof.

3. The composition of claim 1, further comprising a viscosity inducing agent.

4. A pharmaceutical composition formulated for intraocular administration, comprising an adeno-associated virus (AAV), comprising a retinal pigment epithelial-specific promoter, a rod-specific promoter, a cone-specific promoter, or a rod- and cone-specific promoter operably linked to a nucleic acid molecule encoding nuclear factor erythroid 2-like 2 (Nrf2) in an amount effective for prolonging the viability of a photoreceptor cell compromised by a retinal disorder and a pharmaceutically acceptable carrier for intraocular administration, wherein the pharmaceutical composition is formulated for intraocular administration.

5. The composition of claim 1 or 4, wherein the intraocular administration is selected from the group consisting of intravitreal, subretinal, subconjunctival, sub-tenon, periocular, retrobulbar, suprachoroidal, and intrascleral administration.

6. The composition of claim 4, wherein the AAV vector is an AAV 2/5 or an AAV 2/8 vector.

7. The pharmaceutical composition of claim 4, further comprising a viscosity inducing agent.

* * * * *